(12) United States Patent
Fukuhara et al.

(10) Patent No.: US 11,363,857 B2
(45) Date of Patent: Jun. 21, 2022

(54) MOLDED SURFACE FASTENER MANUFACTURING METHOD

(71) Applicant: YKK Corporation, Tokyo (JP)

(72) Inventors: Yoshiyuki Fukuhara, Toyama (JP); Hiroyuki Yamashita, Toyama (JP); Makoto Takekawa, Toyama (JP); Takahiro Fuse, Toyama (JP)

(73) Assignee: YKK Corporation, Tokyo (JP)

( * ) Notice: Subject to any disclaimer, the term of this patent is extended or adjusted under 35 U.S.C. 154(b) by 18 days.

(21) Appl. No.: 16/807,341

(22) Filed: Mar. 3, 2020

(65) Prior Publication Data

US 2020/0196716 A1 Jun. 25, 2020

Related U.S. Application Data

(62) Division of application No. 16/061,887, filed as application No. PCT/JP2016/087982 on Dec. 20, 2016, now Pat. No. 11,291,275.

(30) Foreign Application Priority Data

| Dec. 24, 2015 | (WO) | PCT/JP2015/086076 |
| Apr. 18, 2016 | (WO) | PCT/JP2016/062281 |
| Aug. 2, 2016 | (WO) | PCT/JP2016/072654 |

(51) Int. Cl.
*A44B 18/00* (2006.01)
*B29C 69/02* (2006.01)
(Continued)

(52) U.S. Cl.
CPC ...... *A44B 18/0049* (2013.01); *A44B 18/0007* (2013.01); *A44B 18/0015* (2013.01);
(Continued)

(58) Field of Classification Search
None
See application file for complete search history.

(56) References Cited

U.S. PATENT DOCUMENTS

| 4,454,183 A | 6/1984 | Wollman |
| 5,785,784 A * | 7/1998 | Chesley ............. A44B 18/0049 |
| | | 156/231 |

(Continued)

FOREIGN PATENT DOCUMENTS

| CN | 1232372 A | 10/1999 |
| CN | 1307455 A | 8/2001 |

(Continued)

OTHER PUBLICATIONS

Requirement for Restriction/Election Office Action, U.S. Appl. No. 16/061,979, dated Jan. 10, 2020.

(Continued)

*Primary Examiner* — Robert Sandy
*Assistant Examiner* — Rowland Do
(74) *Attorney, Agent, or Firm* — Kilpatrick Townsend & Stockton LLP

(57) ABSTRACT

In this molded surface fastener, an engaging element includes a columnar stem portion, and micro pawl portions protruding outward from an upper end outer peripheral edge of the stem portion in a plan view of the engaging elements. A pawl width dimension of the micro pawl portions is smaller than a line segment connecting two points on the upper end outer peripheral edge of the stem portion. The micro pawl portions protrude toward a base portion. This molded surface fastener has a high peel strength and a shear strength with respect to a female surface fastener.

2 Claims, 18 Drawing Sheets

(51) Int. Cl.
  *B29C 43/46* (2006.01)
  *B29C 43/22* (2006.01)
  *A61F 13/62* (2006.01)
  *B29C 43/26* (2006.01)
  *B29C 43/52* (2006.01)

(52) U.S. Cl.
  CPC ...... *A44B 18/0019* (2013.01); *A44B 18/0061* (2013.01); *A44B 18/0065* (2013.01); *A44B 18/0073* (2013.01); *A61F 13/625* (2013.01); *B29C 43/222* (2013.01); *B29C 69/02* (2013.01); *B29C 43/52* (2013.01)

(56) References Cited

U.S. PATENT DOCUMENTS

| | | | |
|---|---|---|---|
| 5,879,604 A * | 3/1999 | Melbye | B29C 67/0044 264/167 |
| 5,913,482 A | 6/1999 | Akeno et al. | |
| 5,951,931 A * | 9/1999 | Murasaki | A44B 18/0049 264/167 |
| 5,953,797 A | 9/1999 | Provost et al. | |
| 6,054,091 A | 4/2000 | Miller et al. | |
| 6,162,040 A | 12/2000 | Clune | |
| 6,627,133 B1 | 9/2003 | Puma | |
| 7,350,276 B2 | 4/2008 | Minato et al. | |
| 7,516,524 B2 | 4/2009 | Provost et al. | |
| 8,784,722 B2 | 7/2014 | Rocha | |
| 8,881,369 B2 | 11/2014 | Kirby et al. | |
| 8,961,850 B2 * | 2/2015 | Wood | A44B 18/0065 264/285 |
| 9,210,970 B2 | 12/2015 | Collins et al. | |
| 9,259,060 B2 * | 2/2016 | Cheng | A44B 18/0049 |
| 2001/0022409 A1 | 9/2001 | Parellada et al. | |
| 2002/0190418 A1 | 12/2002 | Jens et al. | |
| 2003/0106188 A1 | 6/2003 | Armela et al. | |
| 2003/0131453 A1 * | 7/2003 | Clarner | A44B 18/0065 24/452 |
| 2004/0031130 A1 | 2/2004 | Clarner et al. | |
| 2004/0031553 A1 | 2/2004 | Berger | |
| 2004/0074071 A1 | 4/2004 | Golden et al. | |
| 2004/0229739 A1 | 11/2004 | Gorman et al. | |
| 2006/0096072 A1 | 5/2006 | Minato et al. | |
| 2007/0063375 A1 | 3/2007 | Tuma | |
| 2010/0306969 A1 | 12/2010 | Seifert | |
| 2013/0067702 A1 | 3/2013 | Tuma | |
| 2015/0010732 A1 | 1/2015 | Tuma | |
| 2015/0275941 A1 | 10/2015 | Nisogi | |
| 2017/0156451 A1 | 6/2017 | Cheng | |
| 2018/0360170 A1 | 12/2018 | Fukuhara et al. | |
| 2018/0368534 A1 | 12/2018 | Fukuhara et al. | |
| 2019/0008239 A1 | 1/2019 | Fukuhara et al. | |
| 2020/0390199 A1 * | 12/2020 | Michihata | A44B 18/00 |

FOREIGN PATENT DOCUMENTS

| | | |
|---|---|---|
| CN | 1336803 A | 2/2002 |
| CN | 1374050 A | 10/2002 |
| CN | 1644357 A | 7/2005 |
| CN | 1798509 A | 7/2006 |
| CN | 102984965 A | 3/2013 |
| CN | 104812262 A | 7/2015 |
| JP | 58-157404 A | 9/1983 |
| JP | 2002-519078 A | 7/2002 |
| JP | 2002-262908 A | 9/2002 |
| JP | 2002-534194 A | 10/2002 |
| JP | 2004-357894 A | 12/2004 |
| JP | 2007-502229 A | 2/2007 |
| JP | 2007-528765 A | 10/2007 |
| JP | 2011-504776 A | 2/2011 |
| JP | 2011-182910 A | 9/2011 |
| JP | 2013-529974 A | 7/2013 |
| JP | 2015-504736 A | 2/2015 |
| WO | 1994/023610 A1 | 10/1994 |
| WO | 1998/014086 A1 | 4/1998 |
| WO | 2000/000053 A1 | 1/2000 |
| WO | 2000/041479 A1 | 7/2000 |
| WO | 2009/149909 A2 | 12/2009 |
| WO | 2011/163193 A1 | 12/2011 |
| WO | 2014/058717 A1 | 4/2014 |
| WO | 2017/110106 A | 6/2017 |

OTHER PUBLICATIONS

European Patent Application No. 15911340.6, Extended European Search Report, dated Apr. 24, 2019, 8 pages.
European Patent Application No. 16878030.2, Extended European Search Report, dated Apr. 29, 2019, 8 pages.
European Patent Application No. 16878714.1, Extended European Search Report, dated Apr. 29, 2019, 9 pages.
Japanese Patent Application No. 2017-557590, Office Action, dated Jun. 4, 2019, 8 pages.
Japanese Patent Application No. 2017-557728, Office Action, dated Jun. 4, 2019, 10 pages.
Japanese Patent Application No. 2017-558167, Office Action, dated Jun. 11, 2019, 6 pages.
Korean Patent Application No. 10-2018-7015786, Office Action, dated Jan. 29, 2019, 20 pages.
Korean Patent Application No. 10-2018-7015787, Office Action, dated Jan. 29, 2019, 21 pages.
Korean Patent Application No. 10-2018-7015788, Office Action, dated Jan. 29, 2019, 17 pages.
International Search Report, PCT Patent Application No. PCT/JP2016/087982, dated Mar. 14, 2017.
Requirement for Restriction/Election Office Action, U.S. Appl. No. 16/061,887, dated Jan. 10, 2020.
International Search Report, PCT Patent Application No. PCT/JP2015/086076, dated Mar. 15, 2016.
International Search Report, PCT Patent Application No. PCT/JP2016/072654, dated Oct. 18, 2016.
Office Action, Chinese Patent Application No. 201680075917.5, dated Dec. 31, 2021, 12 pages.
Office Action, Chinese Patent Application No. 201680075920.7, dated Dec. 30, 2020, 16 pages.
U.S. Appl. No. 16/061,887, Advisory Action, dated Nov. 30, 2020, 3 pages.
U.S. Appl. No. 16/061,979, Supplemental Notice of Allowability, dated Nov. 27, 2020, 2 pages.
U.S. Appl. No. 16/062,038, Advisory Action, dated Nov. 24, 2020, 3 pages.
U.S. Appl. No. 16/061,887, Notice of Allowance, dated Feb. 5, 2021, 8 pages.
U.S. Appl. No. 16/061,887, Final Office Action, dated Sep. 18, 2020, 13 pages.
U.S. Appl. No. 16/061,979, Notice of Allowance, dated Sep. 14, 2020, 9 pages.
U.S. Appl. No. 16/062,038, Final Office Action, dated Sep. 18, 2020, 13 pages.
Decision of Refusal, Japanese Patent Application No. 2017-557728, dated Nov. 28, 2019, 9 pages.
Office Action, Taiwanese Patent Application No. 105140797, dated Sep. 28, 2017, 10 pages.
Office Action, Taiwanese Patent Application No. 105142192, dated Aug. 14, 2017, 19 pages.
Office Action, Taiwanese Patent Application No. 105143110, dated Aug. 23, 2017, 9 pages.
U.S. Appl. No. 16/061,887, Non-Final Office Action, dated Mar. 8, 2021, 13 pages.
U.S. Appl. No. 16/061,979, Notice of Allowance, dated Mar. 10, 2021, 10 pages.
U.S. Appl. No. 16/062,038, Non-Final Office Action, dated Mar. 10, 2021, 13 pages.
U.S. Appl. No. 16/062,038, Notice of Allowance, dated Jul. 22, 2021, 8 pages.
Decision of Refusal, Chinese Patent Application No. 201680075917.5, dated Jun. 23, 2021, 22 pages.
Office Action, Chinese Patent Application No. 201680075920.7, dated Jun. 28, 2021, 13 pages.

(56) References Cited

OTHER PUBLICATIONS

Office Action, Chinese Patent Application No. 201580085530.3, dated Apr. 2, 2020, 14 pages.
U.S. Appl. No. 16/061,887, Non-Final Office Action, dated Mar. 18, 2020, 13 pages.
U.S. Appl. No. 16/061,979, Non-Final Office Action, dated Mar. 19, 2020, 10 pages.
U.S. Appl. No. 16/062,038, Non-Final Office Action, dated Apr. 29, 2020, 16 pages.
Office Action, Chinese Patent Application No. 201680075920.7, dated Apr. 14, 2020, 16 pages.
Office Action, Chinese Patent Application No. 201680075917.5, dated May 28, 2020, 12 pages.
U.S. Appl. No. 16/061,887, Final Office Action, dated Sep. 14, 2021, 12 pages.
U.S. Appl. No. 16/062,038, Notice of Allowance, dated Sep. 24, 2021, 8 pages.
U.S. Appl. No. 16/807,251, Non-Final Office Action, dated Aug. 18, 2021, 9 pages.

* cited by examiner

MOLDED SURFACE FASTENER MANUFACTURING METHOD

This application is a divisional of U.S. Ser. No. 16/061,887, which is incorporated by reference herein in its entirety.

TECHNICAL FIELD

The present invention relates to a molded surface fastener in which a plurality of male engaging elements stand on an upper surface of a flat plate-shaped base portion and a manufacturing method for manufacturing the molded surface fastener.

BACKGROUND ART

Conventionally, surface fastener products in which a female surface fastener having a plurality of loops and a male molded surface fastener which is attachable and detachable with respect to the female surface fastener are used in combination as a pair are known. The male molded surface fastener manufactured by molding synthetic resin, generally, is formed such that a plurality of male engaging elements having a mushroom shape or the like stand on an upper surface of a flat plate-shaped base portion.

The surface fastener products having such a male surface fastener are now broadly used in a wide variety of goods, for example, disposable diapers, infant diaper covers, supporters for protecting joints in limbs, waist corset (lumbago belt), and gloves often used for goods wearable to human bodies.

In a molded surface fastener used for disposable diapers or the like, a J shape, a palm tree shape, a mushroom shape and the like are generally known as typical shapes of male engaging elements. The J-shaped engaging element, for example, protrudes upward from a base portion and has a shape in which an upper end part is curved like a hook. Molded surface fasteners having such a J-shaped engaging element are described in WO 1998/014086 (Patent Document 1: corresponding to JP 2001-501120 A), and the like.

A palm tree-shaped engaging element has a stem portion protruding vertically from a base portion and a hook-shaped engaging head portion extending in a curved manner in two directions opposite to each other from an upper end of the stem portion. Molded surface fasteners having such a palm tree-shaped engaging element are described in U.S. Pat. No. 7,516,524 (Patent Document 2), and the like.

A mushroom-shaped engaging element has a stem portion protruding vertically from a base portion and a disk-shaped engaging head portion integrally formed to be disposed above the stem portion and to bulge outward from an entire upper end outer periphery of the stem portion in a plan view of the engaging element. Molded surface fasteners having such a mushroom-shaped engaging element are described in WO 1994/023610 (Patent Document 3: corresponding to JP 8-508910) and WO 2000/000053 (Patent Document 4: corresponding to JP 2002-519078), and the like.

Further, US Publication 2013/0067702 (Patent Document 5), for example, discloses a molded surface fastener including engaging elements 90 in which a plurality of teeth 93 are provided on an outer peripheral edge part of a disc-shaped engaging head portion 92 as an engaging element with an improved mushroom shape, as shown in FIG. 34, for example. The engaging element 90 of Patent Document 5 shown in FIG. 34 includes a stem portion 91 standing on a base portion, an engaging head portion 92 formed in a disc shape on the stem portion 91, and a plurality of teeth 93 protruding outward from an outer peripheral edge part of the engaging head portion 92. In this case, each tooth 93 provided on the engaging element 90 is protruded from the outer peripheral edge part of the engaging head portion 92 so as to be substantially in parallel with an upper surface of the base portion or to warp upward.

Further, as a modification example in which the engaging head portion is not formed in a disk shape, an engaging element 95 having a shape shown in FIG. 35, for example, is described in Patent Document 5. The engaging element 95 shown in FIG. 35 includes an engaging head portion 97 having a triangular shape in a plan view of the engaging element 95, a tab portion 98 protruding outward from each corner part of the engaging head portion 97, and a plurality of comb portions 99 protruding respectively outward from three side parts of the engaging head portion 97.

PRIOR ART DOCUMENTS

Patent Documents

Patent Document 1: WO 1998/014086
Patent Document 2: U.S. Pat. No. 7,516,524 B2
Patent Document 3: WO 1994/023610
Patent Document 4: WO 2000/000053
Patent Document 5: U.S. 2013/0067702 A1

SUMMARY OF INVENTION

Problems to be Solved by the Invention

When the molded surface fastener having J-shaped engaging elements or palm tree-shaped engaging elements as described above, for example, is engaged with loops of a female surface fastener (a fiber of a nonwoven fabric, for example), the loops hardly come off from the J-shaped or palm tree-shaped engaging elements. For this reason, molded surface fasteners having J-shaped or palm tree-shaped engaging elements have a tendency to have high peel strength against female surface fasteners.

However, in the case of the J-shaped or the palm tree-shaped engaging element, since an upper end part of the engaging element is curved like a hook, an area of the upper end surface (top end surface) of the engaging element is small. Therefore, when touching the upper surface side which becomes the engaging surface of the molded surface fastener, the area to be touched to the skin becomes small. Therefore, in a case when such a molded surface fastener is used for a product to be touched to the skin, such as a disposable diaper or a diaper cover, or a product which requires soft touch feeling, for example, the touch feeling of the product may be sometimes deteriorated.

Further, in the J-shaped or palm tree-shaped engaging element, a base end part or a stem portion standing on a base portion tends to be formed thin. Therefore, when the female surface fastener is strongly pressed against the male molded surface fastener (or the male molded surface fastener is strongly pressed against the female surface fastener) to engage them, the base end part or the stem portion of the engaging element is easy to be bent by pressing force, which may cause a breakage of the molded surface fastener.

On the other hand, in the mushroom-shaped engaging element, since a disk-shaped engaging head portion is formed at an upper end part of the engaging element, an upper end surface of the engaging element can be exposed upward with a larger area compared to the J-shaped or palm tree-shaped engaging element. For this reason, the molded surface fastener having the mushroom-shaped engaging elements has a feature of good texture. Further, since the stem portion of the engaging element is easily formed to be thick, the stem portion is hardly bent even when receiving the pressing force as described above, and the shape of the engaging element can be stably maintained.

Further, when the molded surface fastener having the mushroom-shaped engaging elements is engaged with a nonwoven fabric to be the female surface fastener, the plurality of loops can be engaged stably. However, in the mushroom-shaped engaging element, the upper end part of the engaging element is not curved like a hook as in the J-shape or the palm tree shape.

Therefore, in a case of the mushroom-shaped engaging element, the loop engaged with the engaging element becomes easier to drop out compared with a case of the J-shaped or palm tree-shaped engaging element, and improvement is required. Further, in the engaging element 90 (see FIG. 34) described in the above-described Patent Document 5, a plurality of teeth 93 forming large irregularities are provided on an outer peripheral edge part of the engaging head portion 92. For this reason, there has been a possibility that the molded surface fastener of Patent Document 5 drastically lowers the touch feeling of the molded surface fastener.

Generally, in the male surface fasteners, since engagement rate and peel strength of the loops are easily changed according to the structure, and the like, of the nonwoven fabric to be the female surface fastener, the performance of the male surface fastener may be affected depending on compatibility with the nonwoven fabric. Therefore, it is demanded to have abundant various types of male molded surface fasteners by increasing the variation of the configuration of the engaging elements, and the like, in order to be able to select the male surface fastener according to the nonwoven fabric and the use of the product.

The present invention has been made in view of the above-described conventional problems, and a specific object is to provide a molded surface fastener having a property different from the conventional ones, in that a male engaging element has a new and characteristic configuration. Another object of the present invention is to provide a molded surface fastener capable of having high peel strength with respect to a female surface fastener and obtaining good texture. Further, another object of the present invention is to provide a manufacturing method capable of stably manufacturing a molded surface fastener having a property different from the conventional ones.

Means for Solving the Problems

In order to achieve the above object, a molded surface fastener provided by the present invention is a molded surface fastener made of synthetic resin including a flat plate-shaped base portion and a plurality of engaging elements standing on an upper surface of the base portion, as a basic structure, in which the engaging element includes a columnar stem portion standing on the upper surface of the base portion and at least two micro pawl portions protruding mutually in opposite directions outward from an upper end outer peripheral edge of the stem portion in a plan view of the engaging element on a top end part of the engaging element, a pawl width dimension of the micro pawl portions is set to be smaller than a length of a line segment passing through a center of an upper surface of the stem portion and connecting two points on the upper end outer peripheral edge, and at least one of the micro pawl portions protrudes toward the base portion.

Particularly, in the molded surface fastener of the present invention, it is preferable that a gap is provided between the micro pawl portion and an outer peripheral side surface of the stem portion. It is also preferable that the micro pawl portion protrudes toward the base portion without extending above a height position on an upper surface of a base end part in the micro pawl portion.

It is preferable that the only micro pawl portion is bulged on an outside of the upper end outer peripheral edge of the stem portion in a plan view of the engaging element.

In the molded surface fastener of the present invention, it is preferable that the engaging element includes a rib portion protruded on the upper surface of the stem portion, and that the micro pawl portion protrudes from the rib portion.

Further, in the present invention, the micro pawl portion may protrude from an outer peripheral side surface of the stem portion, and the upper surface of the stem portion and an upper surface of the micro pawl portion may be formed to be a same plane surface.

In such a molded surface fastener of the present invention, it is preferable that a pawl width dimension of the micro pawl portion is set to be a size a half or less of a length of the line segment, and a protrusion length of the micro pawl portion from the upper end outer peripheral edge is set to be a size half or less of a length of the line segment in a plan view of the engaging element.

It is also preferable in the present invention that the columnar stem portion has a frustum shape and that the micro pawl portion is disposed inside of an outer peripheral edge at a base end of the stem portion in a plan view of the engaging element.

Further, it is preferable that an area of each of the micro pawl portions in a plan view of the engaging element is set to be 90% or less of an area of the upper surface of the stem portion in the plan view.

Furthermore, in the present invention, it is preferable that a height dimension of the engaging element from the upper surface of the base portion is set to be 0.05 mm or more and 1.5 mm or less, an upper surface of the stem portion has a circular shape having a diameter of 0.1 mm or more and 0.5 mm or less, or an elliptical shape having a short diameter of 0.1 mm or more and 0.5 mm or less, an outer peripheral edge at a base end of the stem portion in a plan view of the engaging element has a circular shape having a diameter of 0.2 mm or more and 0.6 mm or less, a pawl width dimension of the micro pawl portion is set to be 0.01 mm or more and 0.1 mm or less, a protrusion length of the micro pawl portion from the upper end outer peripheral edge is set to be 0.01 mm or more and 0.1 mm or less in a plan view of the engaging element. In this case, it is preferable that a protruding inclination angle of the micro pawl portion with respect to the outer peripheral side surface of the stem portion is set to be 20° or more and 80° or less, particularly 30° or more and 60° or less, and a gap of 0.01 mm or more and 0.09 mm or less is formed between a tip end of the micro pawl portion and the outer peripheral side surface of the stem portion.

Further, it is preferable that the engaging element is disposed on the upper surface of the base portion at a density of 150 pieces/cm$^2$ or more and 1000 pieces/cm$^2$ or less, and particularly 150 pieces/cm$^2$ or more and 300 pieces/cm$^2$ or less.

Next, a manufacturing method of a molded surface fastener provided by the present invention is a manufacturing method of a molded surface fastener made of synthetic resin in which a plurality of engaging elements stand on an upper surface of a flat plate-shaped base portion, the manufacturing method including a primary molding step for molding a primary molded body including the base portion and a plurality of provisional elements standing on the base portion, being the most primary characterized in that, the method including molding the primary molded body including a columnar stem portion standing on the base portion, a rib portion protruding on an upper surface of the stem portion, and at least two protruded portions protruding from the rib portion toward an outside of an upper end outer peripheral edge of the stem portion along a direction crossing with respect to a standing direction of the stem portion as the provisional element in the primary molding step; and forming the engaging element which includes the stem portion, the rib portion, and micro pawl portions protruding from the rib portion toward the base portion and is capable of engaging loops of a female surface fastener only with the micro pawl portions by deforming the protruded portions of the primary molded body downwardly with respect to the rib portion.

In this case, the above-described manufacturing method of the present invention may further include a secondary molding step of heating at least a part of the micro pawl portions and the rib portion of the engaging element and compressing them from above.

Another manufacturing method of a molded surface fastener provided by the present invention is a manufacturing method of a molded surface fastener made of synthetic resin in which a plurality of engaging elements stand on an upper surface of a flat plate-shaped base portion, the manufacturing method including a primary molding step for molding a primary molded body including the base portion and a plurality of provisional elements standing on the base portion and a secondary molding step for molding the molded surface fastener by heating at least a part of the provisional elements of the primary molded body and compressing them from above, being the most primary characterized in that, the method including molding the primary molded body including a columnar stem portion standing on the base portion, a rib portion protruding on an upper surface of the stem portion, and at least two protruded portions protruding from the rib portion toward an outside of an upper end outer peripheral edge of the stem portion along a direction crossing with respect to a standing direction of the stem portion as the provisional element in the primary molding step; and forming the engaging element which includes a stem portion and micro pawl portions protruding toward the base portion from an outer peripheral side surface of the stem portion and is capable of engaging loops of a female surface fastener only with the micro pawl portions by compressing at least a part of the protruded portions and the rib portion of the primary molded body from above in the secondary molding step.

Each manufacturing method of the present invention as described above preferably includes, molding the primary molded body in the primary molding step using a die wheel provided with an outer side cylindrical body in which a plurality of penetration holes penetrating from an outer peripheral surface to an inner peripheral surface are drilled, and an inner side cylindrical body disposed in close in contact with the inner peripheral surface of the outer side cylindrical body concentrically, in which a plurality of concave groove portions are concaved on an outer peripheral surface of the inner side cylindrical body, and an outer peripheral edge of penetration hole in the inner peripheral surface of the outer side cylindrical body includes a part overlapping and crossing the concave groove portion of the inner side cylindrical body and a part contacting closely with the outer peripheral surface of the inner side cylindrical body.

Effects of the Invention

The molded surface fastener according to the invention includes a flat plate-shaped base portion and a plurality of male engaging elements standing on an upper surface of the base portion. Each engaging element includes a columnar stem portion standing on the base portion and at least two micro pawl portions disposed on a top end part of the engaging element. Further, at least one of the micro pawl portions (preferably all the micro pawl portions) protrudes toward the base portion respectively so as to slope or curve obliquely downward, and protrudes in opposite directions to each other outward from an upper end outer peripheral edge of the stem portion in a plan view of the engaging element from above. A pawl width dimension of each micro pawl portion is set to be smaller than a length of a line segment passing through a center of an upper surface (upper end surface) of the stem portion and connecting two points on an upper end outer peripheral edge. It is preferable that at least one of the micro pawl portions is formed toward the base portion so as to provide a space with an outer peripheral side surface of the stem portion. In a case when the micro pawl portion is formed to be very small or the like, a gap may not be clearly confirmed between the micro pawl portion and the outer peripheral side surface of the stem portion.

Here, a pawl width dimension refers to a dimension of the micro pawl portion in a direction orthogonal to the protruding direction of the micro pawl portion and in a direction orthogonal to an upper and lower direction of the molded surface fastener (standing direction of the stem portion). A line segment to which the pawl width dimension is compared refers to an imaginary straight line of a part passing through a center of an upper surface of the stem portion and connecting two points on an upper end outer peripheral edge of the stem portion in a plan view of the engaging element. The imaginary straight line is orthogonal to the upper and lower direction (the standing direction of the stem portion) of the molded surface fastener.

In particular, in the present invention, the line segment of the imaginary straight line is preferably a line segment along a machine direction (MD: direction in which molded surface fastener flows) in a molding step of the molded surface fastener among the directions orthogonal to the standing direction of the stem portion. Further, in the present invention, when the upper surface of the stem portion of the engaging element has a circular shape parallel to the upper surface of the base portion, a diameter of the circular upper surface of the stem portion corresponds to the line segment of the imaginary straight line. Further, the fact that the two micro pawl portions protrude in opposite directions to each other from the upper end outer peripheral edge of the stem portion in a plan view of the engaging element includes not only a case that the two micro pawl portions are point symmetrical with reference to the center of the upper surface of the stem portion, but also a case that the two micro pawl portions are line symmetrical with reference to the straight line passing through the center of the upper surface of the stem portion.

The engaging element of the present invention including the stem portion and at least two micro pawl portions as described above is provided with a new configuration different from the conventional J shape, the palm tree shape, and the mushroom shape. In the molded surface fastener of the present invention including such an engaging element, it is easy to form the columnar stem portion thick. Therefore, even when a female surface fastener is strongly pressed against the molded surface fastener of the present invention and subjected to a large pressing force, the stem portion is hardly bent and the shape of the engaging element can be stably maintained. In addition, since the stem portion tends to secure a large strength, it is possible to increase a shear strength with respect to the female surface fastener.

Further, in this case, the molded surface fastener of the present invention can be pushed deeply into the female surface fastener. Thereby, each engaging element of the molded surface fastener can be deeply inserted near a root of a loop of the female surface fastener, and the loop can be firmly engaged with the engaging element.

In the present invention, a top surface (upper surface) of the engaging element is formed such that the flat upper surface of the stem portion is exposed upward with a large area. Moreover, in this case, the engaging element is formed such that only the micro pawl portion having a small pawl width dimension only bulges to the outside of the upper end outer peripheral edge of the stem portion in a plan view of the engaging element. Therefore, when the molded surface fastener of the present invention is touched on an upper surface side which is to be the engaging surface, the upper surface of the stem portion tends to be touched widely to the skin. Further, the small micro pawl portion protrudes toward the base portion without extending above a height position of the micro pawl portion at an upper surface of a base end part from the base portion. Therefore, when the engaging element is touched, the influence (discomfort) of the micro pawl portion of the engaging element on its touching comfort can be reduced or eliminated. Accordingly, the molded surface fastener of the present invention can stably obtain better touch feeling and touching comfort than the molded surface fastener having, for example, the J shaped or the palm tree-shaped engaging elements.

Furthermore, in the engaging element of the present invention, at least one (preferably all) of the micro pawl portions disposed on a top end part of the engaging element protrudes toward the base portion. In particular, the micro pawl portion of the present invention protrudes obliquely downward toward the base portion without extending above the height position at the upper surface of the base end part of the micro pawl portion as described above. At the same time, the two micro pawl portions as a pair protrude in opposite directions to each other outward from the upper end outer peripheral edge of the stem portion in a plan view of the engaging element. Therefore, when the loops of the female surface fastener are engaged with the molded surface fastener of the present invention, it is possible to insert the engaging elements of the present invention smoothly between the loops of the female surface fastener, and to hook the loops to the micro pawl portions of the engaging element for stable engagement.

Furthermore, in the engaging element of the present invention, since the micro pawl portions protrude toward the base portion, the loops caught on the micro pawl portions can hardly come off from the engaging elements as compared with the molded surface fastener having the mushroom-shaped engaging elements, for example. Therefore, the molded surface fastener of the present invention are able to have a high peel strength with respect to the female surface fastener.

That is, the molded surface fastener of the present invention has a characteristic configuration which is not seen in the prior art, and is a new type of molded surface fastener having combined a merit of the mushroom-shaped engaging element in which the stem portion is hard to bend and a good texture can be obtained and a merit of the J-shaped or palm tree-shaped engaging element in which a high peel strength with respect to a female surface fastener is provided. Therefore, variations of the molded surface fasteners can be increased by providing the molded surface fastener of the present invention in addition to the conventional molded surface fasteners. As a result, it becomes possible to correspond more properly to various types of female surface fasteners (nonwoven fabric).

In the molded surface fastener of the present invention as described above, the engaging element is formed such that the rib portion is protruded on the upper surface of the stem portion and the two micro pawl portions are protruded toward the base portion from end parts of the rib portion. Thereby, the two micro pawl portions can be stably protruded obliquely downward from the rib portion. In addition, strength of the micro pawl portions can be easily secured.

Further, in the present invention, the engaging element may be formed such that the micro pawl portions protrude from an outer peripheral side surface of the stem portion toward the base portion, and the upper surface of the stem portion and the upper surface of the micro pawl portions are formed to be a same plane surface. Thereby, the upper end surface (top end surface) of the engaging element can be formed to be a wide flat surface. As a result, the texture of the molded surface fastener can be improved.

In the molded surface fastener of the present invention, a pawl width dimension of the micro pawl portion is set to be equal to or less than a half of the length of the line segment of the above-mentioned imaginary straight line, and preferably equal to or less than one third of the length. Further, a protrusion length of the micro pawl portion from the upper end outer peripheral edge of the stem portion is set to be equal to or less than a half of the length of the line segment of the above-mentioned imaginary straight line, and preferably equal to or less than one third of the length. By thus forming the micro pawl portion to be small, the molded surface fastener of the present invention can ensure a high peel strength with respect to the female surface fastener, and can further improve the texture of the molded surface fastener.

Further, in the engaging element of the present invention, the columnar stem portion has a frustum shape, and at the same time, in a plan view of the engaging element, the micro pawl portion is disposed inside of the outer peripheral edge at the base end of the stem portion. Thereby, strength of the stem portion of the engaging element can be stably secured. In addition, good texture of the molded surface fastener can be obtained.

Further, an area of each micro pawl portion in a plan view of the engaging element is set to be 90% or less of an area of an entire upper surface of the stem portion in the plan view at the maximum, preferably 50% or less of the area of the entire upper surface of the stem portion in the plan view, and further preferably 20% or less. In a case that the above described rib portion is provided on the engaging element, the area of the entire upper surface of the stem portion refers to the area of the upper surface of the stem portion including the upper part on which the rib portion of the stem portion is protruded. Since the micro pawl portion is formed to be small as above, the molded surface fastener of the present invention can secure a high peel strength with respect to the female surface fastener. At the same time, the texture of the molded surface fastener can be improved.

Furthermore, in the present invention, a height dimension of the engaging element from the upper surface of the base portion is set to be 0.05 mm or more and 1.5 mm or less. A shape of the upper surface of the stem portion has a circular shape having a diameter of 0.1 mm or more and 0.5 mm or less, or an elliptical shape having a short diameter of 0.1 mm or more and 0.5 mm or less. A shape of an outer peripheral edge of the stem portion at the base end in a plan view of the engaging element has a circular shape having a diameter of 0.2 mm or more and 0.6 mm or less. The pawl width dimension of the micro pawl portion is set to be 0.01 mm or more and 0.1 mm or less. In a plan view of the engaging element, the protrusion length of the micro pawl portion from the upper end outer peripheral edge of the stem portion is set to be 0.01 mm or more and 0.1 mm or less. A protruding inclination angle of the micro pawl portion with respect to the outer peripheral side surface of the stem portion is set to at 20° or more and 80° or less, and preferably 30° or more and 60° or less. A gap of 0.01 mm or more and 0.09 mm or less is formed between a tip end of the micro pawl portion and the outer peripheral side surface of the stem portion. The molded surface fastener in which the engaging elements having the size as above are formed can effectively increase a strength of each engaging element and a peel strength with respect to the female surface fastener. At the same time, the pleasant texture of the molded surface fastener can be stably obtained.

Further, in the molded surface fastener of the present invention, the micro pawl portion of the engaging element is formed to be extremely small. Thus, in the present invention, it is possible to dispose the engaging elements on the upper surface of the base portion at a density of 150 pieces/cm$^2$ or more, and preferably 200 pieces/cm$^2$ or more. The forming density of the engaging elements can be made larger, as compared with a conventional molded surface fastener having mushroom-shaped engaging elements, for example. Thereby, the peel strength against the female surface fastener can be more effectively increased.

On the other hand, the engaging elements are disposed on the upper surface of the base portion at a density of 1000 pieces/cm$^2$ or less, preferably 300 pieces/cm$^2$ or less, and more preferably 280 pieces/cm$^2$ or less, thereby, flexibility of the molded surface fastener can be secured appropriately. Further, when manufacturing the molded surface fastener, the molded surface fastener can be stably molded in a predetermined shape.

Next, the manufacturing method of the present invention for manufacturing the molded surface fastener as described above includes a primary molding step for molding a primary molded body having a base portion and a plurality of provisional elements standing on the base portion. In particular, in the primary molding step of the present invention, the primary molded body including a columnar stem portion standing on the base portion, a rib portion protruding on an upper surface of the stem portion, and at least two micro pawl portions protruding outward from an upper end outer peripheral edge of the stem portion along a direction crossing the standing direction of the stem portion from the rib portion, is molded as at least a part of the provisional element by using a mold member.

After the primary molding step, the molded primary molded body is taken out from the mold member, and the protruded portion of the provisional element is deformed by, for example, its own weight or by an external force such as pressing by a roller or the like and wind pressure or the like, so as to be bent downwardly with respect to the rib portion while the primary molded body is conveyed. Thereby, the molded surface fastener of the present invention provided with the engaging elements which includes the stem portion, the rib portion, and the micro pawl portions protruding obliquely downward from the tip end part of the rib portion toward the base portion and is capable of engaging loops of the female surface fastener only with the micro pawl portions can be efficiently and stably manufactured.

In this case, according to the manufacturing method of the present invention, a secondary molding step of heating at least a part of the micro pawl portions and the rib portion of the engaging element, as well as compressing them from above, can be further conducted with respect to the molded surface fastener including the engaging element in which the micro pawl portions protrude toward the base portion. Thereby, it is possible to efficiently and stably manufacture the molded surface fastener of the present invention provided with the engaging elements which include the stem portion, and the micro pawl portions protruding obliquely downward from the outer peripheral side surface of the stem portion and is capable of engaging loops of the female surface fastener only with the micro pawl portions. Further, since the engaging element can be molded so as to expand in a width direction, further improvement of the engaging strength can be at least expected. Furthermore, since the upper surface of the engaging element is squashed in the secondary molding step, it also can be expected that the upper surface is planarized and the upper surface of the stem portion and the upper surface of the micro pawl portions are formed to be the same plane surface.

Another manufacturing method of the molded surface fastener according to the present invention includes a primary molding step for molding a primary molded body including a base portion and a plurality of provisional elements standing on the base portion and a secondary molding step for molding the molded surface fastener by heating at least a part of the provisional elements of the primary molded body and compressing them from above.

In particular, in the primary molding step of the present invention, a primary molded body including a columnar stem portion standing on the base portion, a rib portion protruding on the upper surface of the stem portion, and at least two micro pawl portions protruding outward from an upper end outer peripheral edge of the stem portion along a direction crossing with respect to the standing direction of the stem portion from the rib portion as at least a part of the provisional elements, by using a mold member.

Furthermore, in the secondary molding step of the present invention, the provisional element can be deformed by compressing at least a part of the micro pawl portion and the rib portion of the primary molded body taken out from the mold member from above. Accordingly, the molded surface fastener of the present invention provided with the engaging element which includes the stem portion and the micro pawl portions protruding from the outer peripheral side surface of the stem portion toward the base portion, and is capable of engaging loops of the female surface fastener only with the micro pawl portion, can be efficiently and stably manufactured. Further, since the engaging element can be formed so as to expand in a width direction, engaging strength can be further improved. In addition, it is also expected that the upper surface of the engaging element is planarized and the upper surface of the stem portion and the upper surface of the micro pawl portion are formed to be a same plane surface by this secondary molding step.

In each manufacturing method of the present invention described above, in the primary molding step, molding the primary molded body is conducted by using a die wheel provided with an outer side cylindrical body in which a plurality of penetration holes penetrating from an outer peripheral surface to an inner peripheral surface are drilled and an inner side cylindrical body disposed closely contacting on an inner peripheral surface of the outer side cylindrical body are provided concentrically as a mold member, a plurality of concave groove portions are concaved on an outer peripheral surface of the inner side cylindrical body, and an outer peripheral edge of the penetration hole on the inner peripheral surface of the outer side cylindrical body has a part overlapping and crossing the concave groove portion of the inner side cylindrical body and a part contacting closely with the outer peripheral surface of the inner side cylindrical body. Thereby, it is possible to form the primary molded body having the plurality of provisional elements effectively and stably, and to form a molding apparatus of the primary molded body having a simple structure.

MODES FOR CARRYING OUT THE INVENTION

Hereinafter, modes for carrying out the invention favorably will be described in detail showing embodiments with reference to the drawings. It should be noted that the present invention is not limited to the embodiments explained as below, and various changes can be made as long as having a substantially same structure and similar functional effects. In the following embodiments, for example, the number, an arrangement position, a forming density, and the like of the male engaging elements disposed on the base portion of the molded surface fastener are not particularly limited, and can be changed arbitrarily.

Embodiment 1

Figure 1:
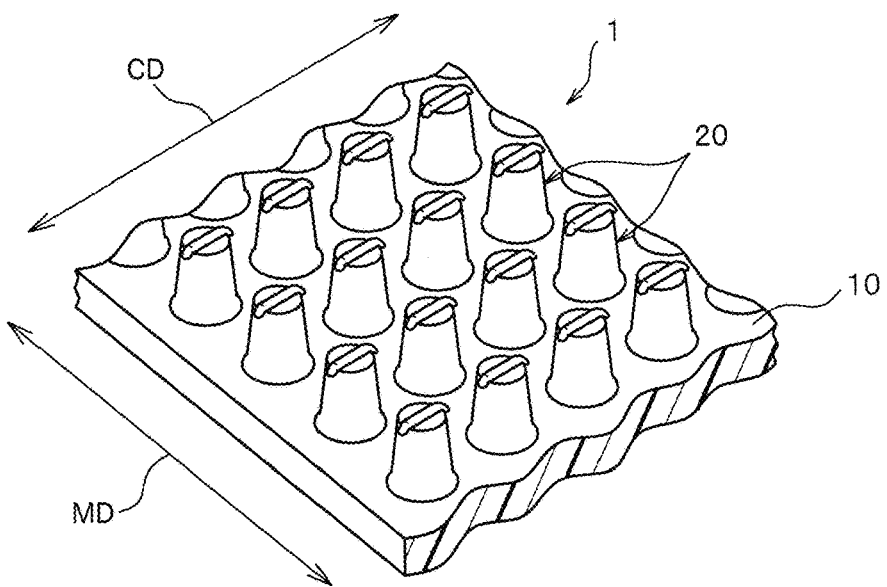
FIG. 1 is a perspective view illustrating a molded surface fastener according to Embodiment 1 of the present invention.
Figure 2:
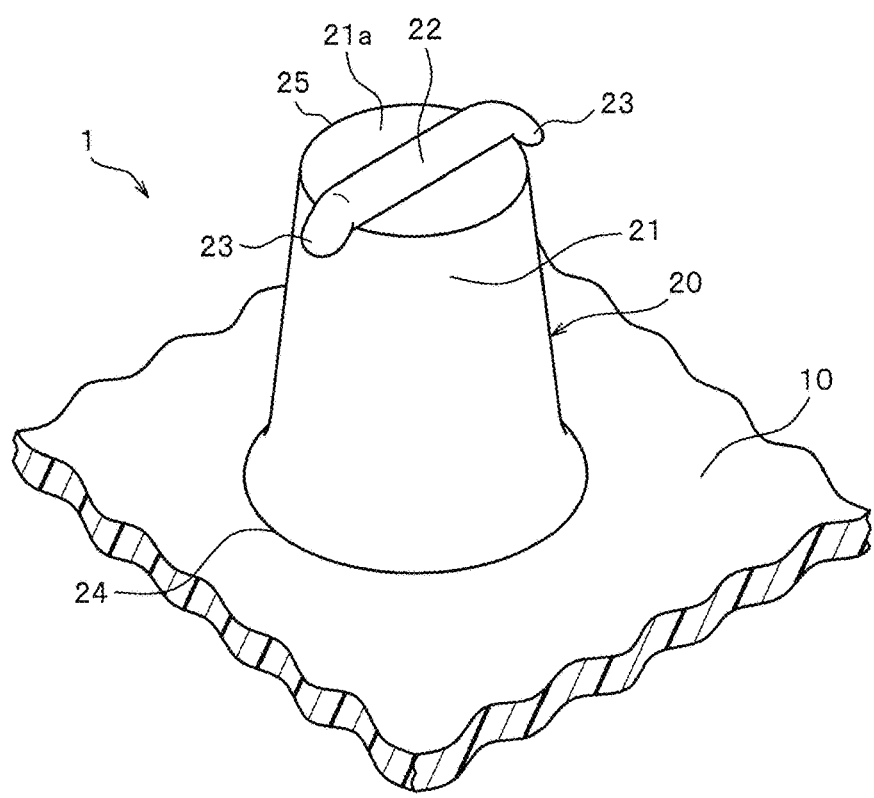
FIG. 2 is a perspective view illustrating an engaging element of the molded surface fastener.
Figure 6:
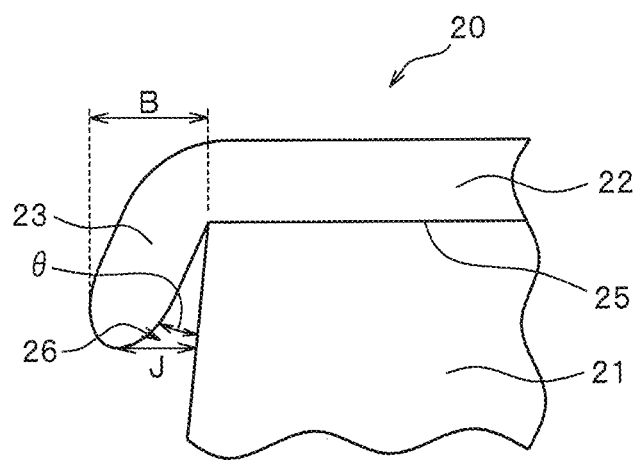
FIG. 6 is an enlarged front view enlarging a micro pawl portion of the engaging element.

FIG. 1 is a perspective view illustrating a molded surface fastener according to Embodiment 1. FIGS. 2-5 are views of an engaging element of the molded surface fastener when viewed from various directions. FIG. 6 is an enlarged view enlarging a micro pawl portion disposed on the engaging element.

In the following descriptions, a front and rear direction regarding a molded surface fastener and a primary molded body is defined as a length direction of the molded surface fastener and a primary molded body to be molded long as described later, and as a direction along a machine direction (M direction or MD) through which the molded surface fastener or the primary molded body flows in a manufacturing step of the molded surface fastener.

A right and left direction is a width direction orthogonal to a length direction and along an upper surface (or lower surface) of the base portion of the molded surface fastener. In this case, the right and left direction and the width direction can also be defined as an orthogonal direction (C direction or CD) orthogonal to the machine direction (MD). An upper and lower direction (thickness direction) is a height direction orthogonal to a length direction and orthogonal to an upper surface (or lower surface) of the base portion of the molded surface fastener.

The molded surface fastener 1 of the Embodiment 1 shown in FIG. 1 is manufactured by molding a thermoplastic resin using a manufacturing apparatus 30 provided with a molding apparatus 31 or a manufacturing apparatus 30a provided with a molding apparatus 31a as described later. The molded surface fastener 1 is formed to have a rectangular sheet shape long in a machine direction of the manufacturing apparatus 30 or the manufacturing apparatus 30a in a plan view. In the present invention, a length dimension and a width dimension of the molded surface fastener 1 are not particularly limited. By cutting the molded surface fastener 1, the size of the molded surface fastener 1 can be arbitrarily changed. Further, the molded surface fastener 1 may have a shape other than a rectangle in a plan view.

The kinds of synthetic resin forming the molded surface fastener 1 are also not particularly limited. As a material of the molded surface fastener 1 in the present invention, a thermoplastic resin such as polypropylene, polyester, nylon, polybutylene terephthalate, or a copolymer thereof can be adopted. The molded surface fastener 1 of the Embodiment 1 is made of polypropylene.

The molded surface fastener 1 of the Embodiment 1 includes a thin plate-shaped base portion 10 and a plurality of engaging elements 20 standing on an upper surface of the base portion 10. The base portion 10 is formed to have a predetermined thickness, and the upper surface and a lower surface of the base portion 10 are flat and formed parallel to each other.

The plurality of engaging elements 20 are disposed to be aligned regularly along a machine direction (MD) and an orthogonal direction (CD). In the present invention, the arrangement pattern of the engaging elements 20 is not limited. For example, the plurality of engaging elements 20 may be regularly arranged in another arrangement pattern such as a zigzag on the upper surface of the base portion 10, or may be provided randomly on the upper surface of the base portion 10.

Each engaging element 20 of the Embodiment 1 includes a stem portion 21 standing on the base portion 10, a rib portion 22 protruding on an upper end surface 21a of the stem portion 21 along a right and left direction (CD), and a right and left pair of micro pawl portions 23 protruding outward from right and left side end edges of the rib portion 22, respectively.

The stem portion 21 of the engaging element 20 is formed upright from the base portion 10 in a direction orthogonal to the upper surface of the base portion 10. The stem portion 21 has a frustum shape such that an area of a cross section orthogonal to an upper and lower direction gradually increases as approaching the base portion 10. In particular, a lower end part of the stem portion 21 of the Embodiment 1 is formed such that the outer peripheral side surface curves outwardly downward. In this case, the cross-sectional shape of the stem portion 21 cut along a surface parallel to the upper surface of the base portion 10 shows a circular shape when the stem portion 21 is cut at any height position.

The stem portion 21 has the above-described configuration, thereby, it is possible to have such a high strength that deformation such as breakage of the stem portion 21 hardly occurs, even when a nonwoven fabric serving as a female surface fastener is pressed strongly toward the molded surface fastener 1 of the Embodiment 1, for example.

Figure 3:
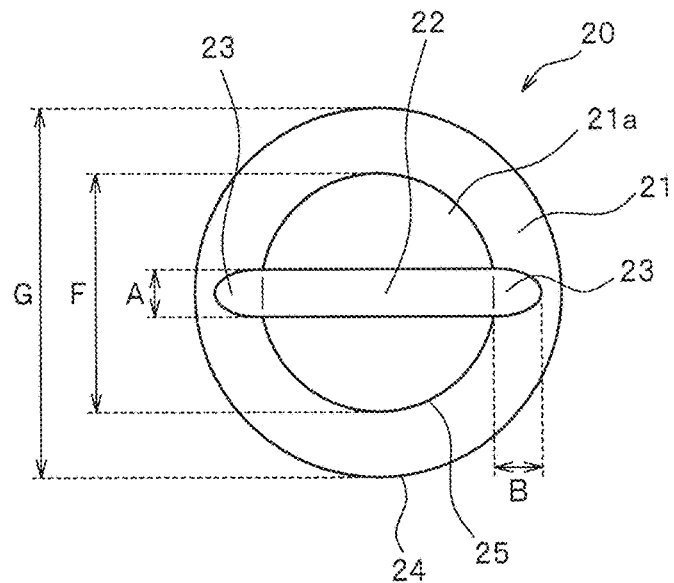
FIG. 3 is a plan view illustrating the engaging element only.

The upper end surface 21a of the stem portion 21 is formed to be a flat surface parallel to the upper surface of the base portion 10 and having a circular shape in a plan view of the engaging element 20 (FIG. 3). As a result, the upper end surface 21a of the stem portion 21 excluding the part provided with the rib portion 22 can be exposed widely upward as the upper surface of the engaging element 20. In this case, the upper surface of the engaging element 20 is formed of the upper end surface 21a of the stem portion 21 and the curved upper surface of the rib portion 22. Therefore, when the molded surface fastener 1 of the Embodiment 1 is touched from above, the flat upper end surface 21a of the stem portion 21 can be easily touched to the skin.

As a result, in the molded surface fastener 1 of the Embodiment 1, as compared with the conventional molded surface fastener having, for example, a J-shaped or palm tree-shaped engaging element with a small upper end surface area, the upper surface side which becomes the engaging surface has a smooth (or soft) and pleasant texture. Although the rib portion 22 is bulged from the upper end surface 21a of the stem portion 21, the rib portion 22 provided in the Embodiment 1 is extremely small, and the upper surface of the rib portion 22 is formed to be a curved surface with no corners as described later. Therefore, the influence of the rib portion 22 on the touch comfort of the molded surface fastener 1 is extremely small.

An outer peripheral edge 24 at a base end (lower end) of the stem portion 21 connected to the base portion 10 has a circular shape having a larger diameter than the circular shape exhibited by the upper end surface 21a of the stem portion 21 in a plan view of the engaging element 20. In this case, a circular upper end outer peripheral edge 25 serving as a boundary (ridge line) between the upper surface and the outer peripheral side surface of the stem portion 21 and the circular outer peripheral edge 24 at the base end of the stem portion 21 are disposed concentrically in a plan view. In the present invention, the configuration of the stem portion 21 is not limited to the frustum shape as described above. The stem portion 21 may have a truncated pyramid shape such as a truncated square pyramid shape or a prismatic shape such as a columnar shape or a quadrangular prism shape, for example. In the present invention, the stem portion 21 may have any shape as long as it has a configuration extending upward (standing) from the base portion 10, and a shape having such a configuration is expressed as "columnar".

The rib portion 22 of the Embodiment 1 has a single rod-shaped configuration along the right and left direction (CD). The rib portion 22 bulges upward from the circular upper end surface 21a of the stem portion 21 and is disposed along a diameter of the circular upper end surface 21a of the stem portion 21. The upper surface of the rib portion 22 is formed as a curved surface curving upward in a convex shape along the front and rear direction (MD). A cross section orthogonal to the right and left direction (CD) of the rib portion 22 has a substantially U-shape or semicircular shape having a round shape upward. In addition, the cross section of such a rib portion 22 has the same shape throughout the entire right and left direction of the rib portion 22.

In the Embodiment 1, a dimension in a front and rear direction of the rib portion 22 in a plan view of the engaging element 20 is referred to as a rib width dimension. This rib width dimension has the same size as a pawl width dimension A at a base end part of the micro pawl portion 23, as described later. In this case, the rib width dimension is set to be a size ⅒ or more and ½ or less of a dimension in the front and rear direction of the circular upper end surface 21a of the stem portion 21 (that is, the diameter of the circular upper end surface), preferably ⅛ or more and ⅓ or less, and further preferably ⅙ or more and ¼ or less. Such a rib portion 22 is provided, thereby, it is possible to stably mold the micro pawl portion 23 having a minute size in the manufacturing step of the molded surface fastener 1. Further, it is possible to stably secure strength of the micro pawl portion 23.

The right and left micro pawl portions 23 provided at a top end part (upper end part) of each engaging element 20 are formed to be bent from right and left side end edges of the rib portion 22 toward the base portion 10 such that tips of the pawls hang downward. In other words, the micro pawl portion 23 protrudes so as to slope obliquely downward from the right and left side end edges of the rib portion 22 toward the base portion 10, without extending above a height position of the upper surface of the base end part connected to the rib portion 22 in the micro pawl portions 23 (that is, the height position of the upper surface of the rib portion 22). Thereby, a gap 26 is formed between the micro pawl portion 23 and the outer peripheral side surface of the stem portion 21. It should be noted that the micro pawl portion 23 of the Embodiment 1 may protrude in a curved shape curving obliquely downward from the right and left side end edges of the rib portion 22 toward the base portion 10. Further, the micro pawl portion 23 may be declined even slightly toward the upper surface of the base portion 10.

The two micro pawl portions 23 of the Embodiment 1, in a plan view of the engaging element, protrude in opposite directions to each other outward from a position of the circular upper end outer peripheral edge 25 of the stem portion 21 along a radial direction of the circular upper end surface 21a of the stem portion 21 in a plan view of the engaging element 20. In this case, the right and left micro pawl portions 23 are disposed point symmetrically based on the center of the upper end surface 21a of the stem portion 21 in a plan view of the engaging element 20. In the engaging element 20 of the Embodiment 1, there is nothing bulging outward from the upper end outer peripheral edge 25 of the upper end surface 21a of the stem portion 21, except for the two micro pawl portions 23. That is, any engaging component for engaging loops other than the micro pawl portion 23 is not molded from the stem portion 21.

Each of the right and left micro pawl portions 23 is formed to be circular as a whole and to have a shape to become thinner toward a pawl tip end. That is, the pawl tip end portion of the micro pawl portion 23 has a tapered shape in which the pawl width dimension of the micro pawl portion 23 gradually decreases toward the pawl tip end. Further, an outer surface visible from the upper side of the micro pawl portion 23 is formed to be a curved surface so as to smoothly curve from the base end part of the micro pawl portion 23 toward the pawl tip end, and to smoothly curve along the pawl width direction (the front and rear direction in the Embodiment 1) in a convex shape upward.

In the Embodiment 1, the upper end surface 21a of the stem portion 21 is parallel to the upper surface of the base portion 10 and has a flat circular shape. Therefore, the line segment, defined by the present invention, of the imaginary straight line passing through a center of the upper surface of the stem portion 21 and connecting two points on the upper end outer peripheral edge of the stem portion 21 corresponds to a diameter of the circular upper end surface 21a of the stem portion 21 in the Embodiment 1.

In this case, the pawl width dimension A at the base end part of the micro pawl portion 23 is set at a size ½ or less of the diameter of the circular upper end surface 21a of the stem portion 21 (in particular, the diameter along the front and rear direction), preferably ⅓ or less, and further preferably ¼ or less. Thus, although the micro pawl portion 23 is protruded, the influence of the micro pawl portion 23 on the texture of the molded surface fastener 1 can be suppressed to a small extent.

The pawl width dimension A at the base end part of the micro pawl portion 23 is set at a size ⅒ or more of the diameter of the circular upper end surface 21a of the stem portion 21, preferably ⅛ or more, and further preferably ⅙ or more. Thereby, strength of the micro pawl portion 23 can be stably secured. Further, when engaging the female surface fastener with the molded surface fastener 1 of the Embodiment 1, the loop of the female surface fastener can be stably hooked to the micro pawl portion 23 of the engaging element 20.

When the shape of the upper end surface of the stem portion is not a circular shape as in the Embodiment 1 but a polygonal shape such as a quadrangular shape, for example, a length of the line segment passing through the center of the upper end surface of the stem portion and connecting two points on the upper end outer peripheral edge of the stem portion depends on a direction of the line segment. Therefore, the line segment in the case when the upper surface shape of the stem portion is a polygon refers to a line segment oriented along the front and rear direction (MD). Further, when the direction of the front and rear direction (MD) in the molded surface fastener is unknown, for example, the line segment in the case when the upper surface shape of the stem portion is a polygon refers to a line segment in the direction having the largest length dimension.

In a plan view of the engaging element 20 (FIG. 3) of the Embodiment 1, the right and left micro pawl portions 23 are disposed within a donut-shaped region between the circular upper end outer peripheral edge 25 on the upper surface of the stem portion 21 and a circular outer peripheral edge 24 at the base end of the stem portion 21.

In this case, in a plan view of the engaging element 20, a protrusion length B of the micro pawl portion 23 along the radial direction of the upper surface of the stem portion 21 from the circular upper end outer peripheral edge 25 of the stem portion 21 to the pawl tip end of the micro pawl portion 23 is set at a size ½ or less of the diameter of the circular upper end surface 21*a* of the stem portion 21, preferably ⅓ or less, and further preferably ¼ or less. Thereby, although the micro pawl portion 23 is protruded, the influence of the micro pawl portion 23 on the texture of the molded surface fastener 1 can be reduced.

In the Embodiment 1, a specific size of the engaging element 20 is set as follows.

For example, a height dimension C of the engaging element 20 in an upper and lower direction from the upper surface of the base portion 10 is set to be 0.05 mm or more and 1.5 mm or less, and preferably 0.2 mm or more and 1.0 mm or less. In this case, a height dimension D of the stem portion 21 from the upper surface of the base portion 10 is set to be 0.04 mm or more and 1.5 mm or less, and preferably 0.2 mm or more and 1.0 mm or less. A height dimension E of the rib portion 22 is set to be 0.01 mm or more and 0.1 mm or less.

A diameter F at the circular upper end surface 21*a* of the stem portion 21 is set to be 0.1 mm or more and 0.5 mm or less. When the upper end surface of the stem portion is a polygonal shape in a plan view, for example, the line segment along the front and rear direction (MD) passing through the center of the upper end surface of the stem portion and connecting two points on the upper end outer peripheral edge of the stem portion is set to 0.1 mm to 0.5 mm. A diameter G at the circular outer peripheral edge of the stem portion 21 at the base end is not less than the above diameter F and is set to be 0.15 mm or more and 0.55 mm or less.

Regarding the micro pawl portion 23 of the Embodiment 1, a pawl width dimension A of the micro pawl portion 23 is set to be 0.01 mm or more and 0.1 mm or less, and preferably 0.03 mm or more and 0.08 mm or less. In this case, the rib width dimension of the rib portion 22 (the maximum value of the dimension in the front and rear direction in the Embodiment 1) is the same as the pawl width dimension A of the micro pawl portion 23, and is set to be 0.01 mm or more and 0.1 mm or less.

In a plan view of the engaging element 20, the protrusion length B of the micro pawl portion 23 is set to be 0.01 mm or more and 0.1 mm or less. The pawl height dimension H of the micro pawl portion 23 in the upper and lower direction from the upper surface of the rib portion 22 to the pawl tip end of the micro pawl portion 23 is set to be 0.01 mm or more and 0.1 mm or less.

A size J of the gap 26 formed between the micro pawl portion 23 and the outer peripheral side surface of the stem portion 21 at the height position of the pawl tip end of the micro pawl portion 23 is set to be 0.01 mm or more and 0.09 mm or less. A protruding inclination angle θ of the micro pawl portion 23 formed by the pawl back surface of the micro pawl portion 23 and the outer peripheral side surface of the stem portion 21 is larger than 0°, preferably 20° or more and 80° or less, and further preferably 30° more and 60° or less.

An area of the circular upper end surface 21*a* of the stem portion 21 (including the upper surface portion where the rib portion is formed) is set to 0.01 $mm^2$ to 0.25 $mm^2$. The area of the micro pawl portion 23 which can be confirmed in a plan view of the engaging element 20 is set to 0.005 $mm^2$ to 0.05 $mm^2$ and is set to 90% or less, preferably 50% Or less, and further preferably 20% or less, of the area of the circular upper end surface 21*a* of the stem portion 21.

In the molded surface fastener 1 of the Embodiment 1, the engaging element 20 having the extremely small micro pawl portion 23 as described above is not provided with a coupling head portion such as a conventional mushroom-shaped engaging element. Therefore, the circular outer peripheral edge 24 at the base end of the stem portion 21 is located furthest away from the center of the engaging element 20 (the center of the stem portion 21), in a plan view of the engaging element 20 of the Embodiment 1, as shown in FIG. 3. In other words, all of the stem portion 21, the rib portion 22, and the two micro pawl portions 23 of the engaging element 20 are located inside the circular outer peripheral edge 24 at the base end of the stem portion 21 in a plan view of the engaging element 20.

Therefore, in the molded surface fastener 1 of the Embodiment 1, an interval between the adjacent engaging elements 20 can be set without considering the size of the coupling head portion, for example, as in the conventional mushroom-shaped engaging element 20. Thereby, in the molded surface fastener 1 of the Embodiment 1, as compared with the molded surface fastener having a conventional mushroom-shaped engaging element, for example, the interval between the adjacent engaging elements 20 can be made small, and the forming density of the engaging elements 20 can be increased.

Specifically, in the case of the Embodiment 1, the interval between the engaging elements 20 adjacent to each other in the front and rear direction (MD) and the interval between the engaging elements 20 adjacent to each other in the right and left direction (CD) can be set to 0.8 mm or less, preferably 0.6 mm or less, and further preferably 0.5 mm or less. Therefore, the forming density of the engaging elements 20 on the upper surface of the base portion 10 can be increased to 150 pieces/$cm^2$ or more, and preferably 200 pieces/$cm^2$ or more.

As described above, in the molded surface fastener 1 of the Embodiment 1, the engaging elements can be provided at higher density as compared with the conventional molded surface fastener having each of the mushroom-shaped engaging elements 20, for example. Since the number of engaging elements 20 to be disposed per unit area can be increased in this manner, it is possible to effectively enhance a peel strength of the molded surface fastener 1 with respect to the female surface fastener. This makes it possible to obtain a high peel strength even when the area (effective engaging area) of the engaging region of the molded surface fastener 1 on which the engaging elements 20 stand is reduced, for example. However, in another configuration, at least one of the two micro pawl portions 23 of the engaging element 20 may be disposed outside the circular outer peripheral edge 24 at the base end of the stem portion 21 in a plan view of the engaging element 20.

On the other hand, in the Embodiment 1, the interval between the engaging elements 20 adjacent to each other in the front and rear direction (MD) and the interval between the engaging elements 20 adjacent to each other in the right and left direction (CD), are preferably set to be 0.3 mm or more, and particularly 0.35 mm or more. Further, the forming density of the engaging elements 20 on the upper surface of the base portion 10 is set to be 1000 pieces/cm$^2$ or less, preferably 300 pieces/cm$^2$ or less, and more preferably 280 pieces/cm$^2$ or less. Since the engaging elements 20 are provided in such a density range, flexibility of the molded surface fastener 1 can be appropriately secured. In addition, when manufacturing the molded surface fastener 1, it is possible to mold the molded surface fastener 1 stably in a predetermined shape. Further, it is possible to prevent that the loops of the female surface fastener are hard to be hooked due to excessive number of the engaging elements 20.

In the molded surface fastener 1 of the Embodiment 1, the above-described engaging elements 20 shown in FIGS. 1 to 6 stand on the base portion 10. However, in the present invention, it is not necessary for all the engaging elements 20 standing on the base portion 10 to have the same shape.

For example, since the size of each of the engaging elements 20 in the present invention is extremely small, it is sometimes difficult to uniform all the engaging elements 20 in the same shapes. Further, when manufacturing the molded surface fastener 1 using a mold member, for example, although the engaging elements 20 are molded from molding cavities with the same shape, the shape of the engaging elements 20 (particularly the shape of the micro pawl portions 23) may be different from other engaging elements 20.

Therefore, in the present invention, it is sufficient that a part of the engaging elements 20 among all the engaging elements 20 standing on the base portion 10 is the engaging element 20 having the features of the present invention. In this case, it is sufficient that the engaging elements 20 having the features of the present invention are formed at a ratio of 10% or more of the number of all the engaging elements 20 standing on the base portion 10, preferably 25% or more, and particularly preferably 50% or more.

Figure 7:
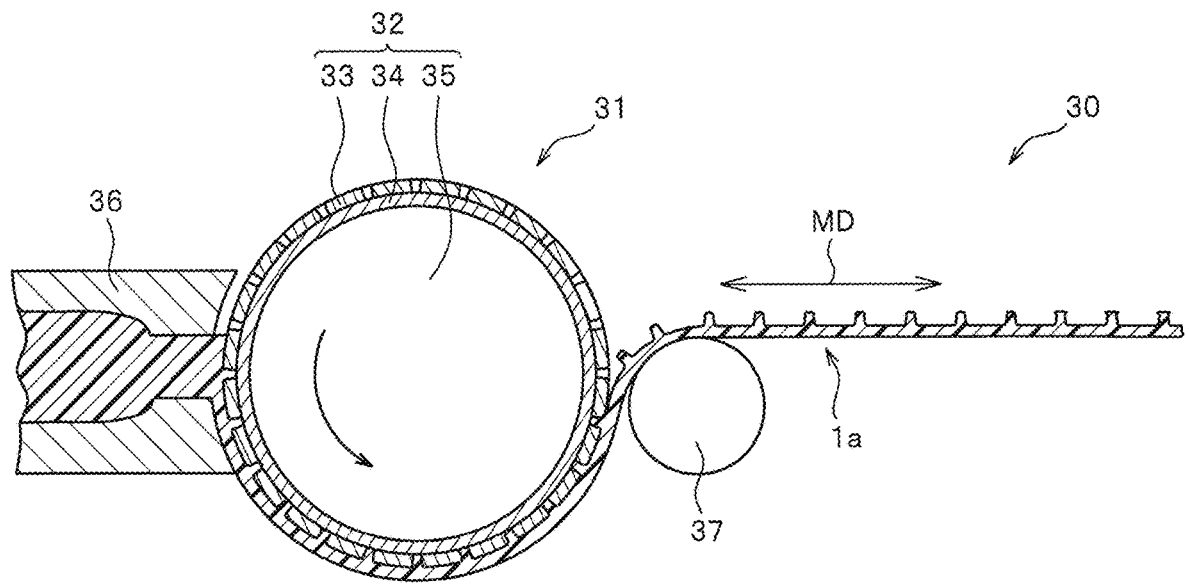
FIG. 7 is a schematic view schematically illustrating a molding apparatus of the molded surface fastener in Embodiment 1.

The molded surface fastener 1 of the Embodiment 1 as described above is manufactured using the manufacturing apparatus 30 as shown in FIG. 7.

The manufacturing apparatus 30 includes a molding apparatus 31 for conducting a primary molding step and a conveying apparatus (not shown) for cooling while conveying the primary molded body 1a molded in the primary molding step.

The molding apparatus 31 of the Embodiment 1 includes a die wheel 32 rotating and driving in one direction (counterclockwise direction in the drawings), an extrusion nozzle 36 which is disposed to face a circumferential surface of the die wheel 32 and extruding continuously a molten synthetic resin material, and a pickup roller 37 disposed on a downstream side of the extrusion nozzle 36 in a rotation direction of the die wheel 32.

The die wheel 32 is provided with a cylindrical outer side cylindrical body (outside sleeve) 33 to be a mold member, a cylindrical inner side cylindrical body (inside sleeve) 34 disposed in close contact with an inside of the outer side cylindrical body 33, and a rotation driving roller 35 for rotating the outer side cylindrical body 33 and the inner side cylindrical body 34 in one direction.

In this case, the die wheel 32 includes a double cylindrical structure in which the outer side cylindrical body 33 and the inner side cylindrical body 34 are concentrically rotatably disposed. Further, a cooling jacket (not shown) for circulating cooling liquid is provided inside the rotation driving roller 35, so that the primary molded body 1a molded on a peripheral surface of the die wheel 32 can be efficiently cooled.

Figure 8:
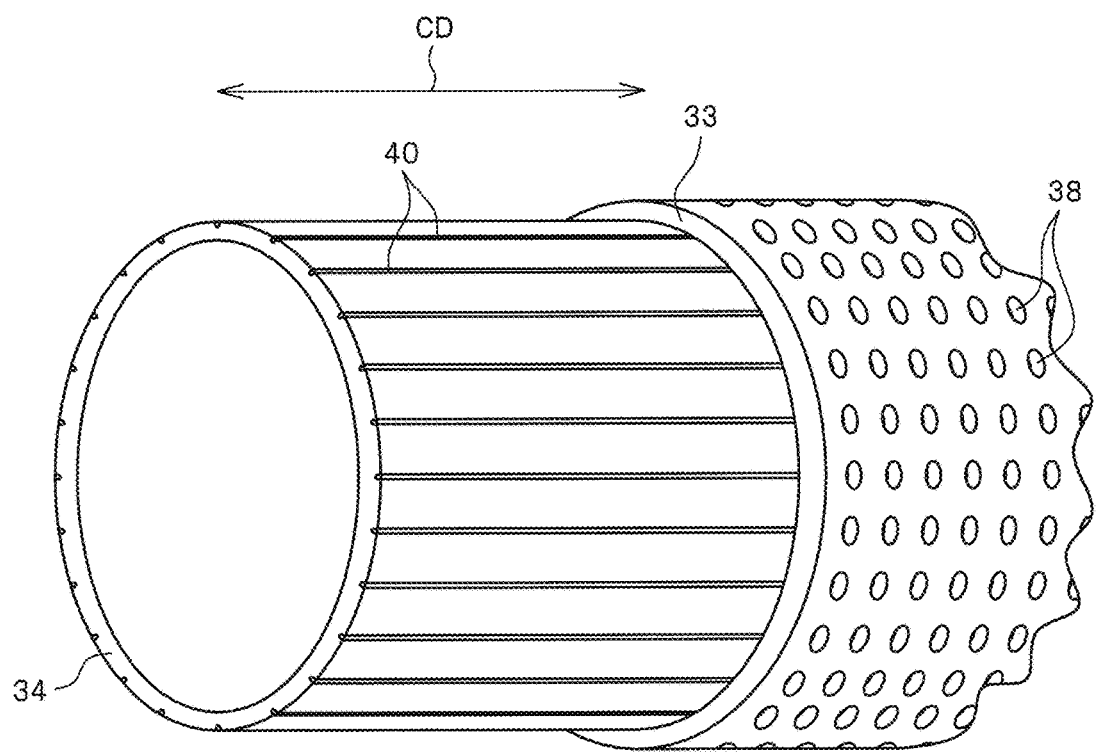
FIG. 8 is a perspective view schematically illustrating an outer side cylindrical body and an inner side cylindrical body of the molding apparatus.
Figure 9:
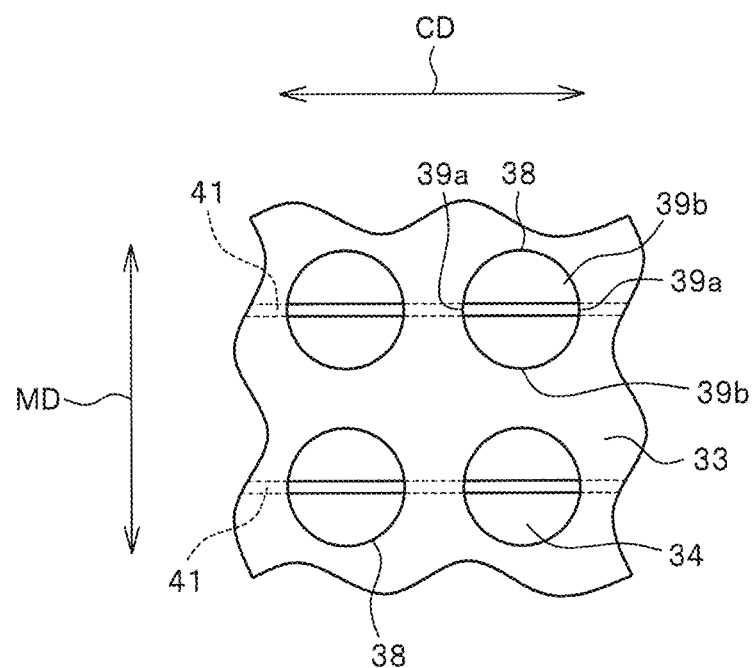
FIG. 9 is a schematic view of a main part illustrating a positional relationship between a penetration hole formed on the outer side cylindrical body and a concave groove portion provided on the inner side cylindrical body.
Figure 10:
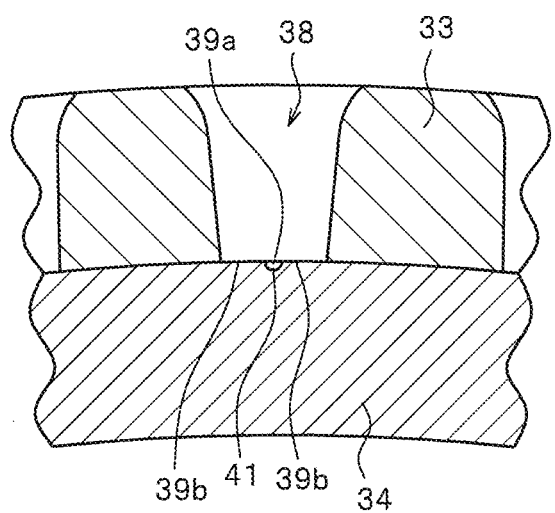
FIG. 10 is a cross-sectional view illustrating a cross section of the outer side cylindrical body and the inner side cylindrical body.

As shown in FIGS. 8 to 10, a plurality of penetration holes 38 penetrating from the outer peripheral surface to the inner peripheral surface of the outer side cylindrical body 33 are provided on the outer side cylindrical body 33 of the die wheel 32 as a cavity for molding the stem portion 21 of the primary molded body 1a as described later. These plurality of penetration holes 38 are formed corresponding to the arrangement position of the engaging elements 20 of the molded surface fastener 1 to be manufactured. In the case of the Embodiment 1, the penetration holes 38 are formed at predetermined pitches in the circumferential direction that is an M direction (MD) of the outer side cylindrical body 33, and are formed in a C direction (CD) parallel to a central axis of the outer side cylindrical body 33 at predetermined pitches. Each of the penetration holes 38 has a frustum shape in which a circular shape of the outer peripheral surface of the outer side cylindrical body 33 is formed larger than a circular shape of the inner peripheral surface of the outer side cylindrical body 33.

The outer side cylindrical body 33 of the Embodiment 1 as above is formed by producing a cylindrical primary outer side cylindrical body and subsequently drilling a plurality of penetration holes 38 in a predetermined position in the primary outer side cylindrical body. In this case, the primary outer side cylindrical body is made of a conventionally known metal such as nickel, stainless steel or the like.

Further, the outer side cylindrical body 33 is preferably formed seamlessly, and can be manufactured by electrocasting or rolling, for example. Further, a known technique can be used for a processing method of the plurality of penetration holes 38. Laser, electron beam, machining, etching, drilling can be used, for example. In the present invention, the method of forming the outer side cylindrical body 33, the size of the outer side cylindrical body 33, and the shape and arrangement of the penetration holes 38 are not particularly limited.

A plurality of concave groove portions 41 are formed on the outer peripheral surface of the inner side cylindrical body 34 of the Embodiment 1. The concave groove portions 41 of the inner side cylindrical body 34 can also be produced by using the same method as in the case of producing the penetration holes 38 on the outer side cylindrical body 33.

The concave groove portions 41 are linearly concaved along the C direction (CD) parallel to the central axis of the cylinder of the inner side cylindrical body 34. The concave groove portion 41 has a groove width and a groove depth which allow the synthetic resin forming the molded surface fastener 1 to flow in a molten state. In the case of the Embodiment 1, the concave groove portions 41 of the inner side cylindrical body 34 are formed with a predetermined pitch in the circumferential direction which is the M direction so as to overlap with the diameter of the penetration holes 38 formed on the outer side cylindrical body 33.

In the Embodiment 1, a forming pitch in the circumferential direction of the penetration holes 38 provided on the outer side cylindrical body 33 and a forming pitch in the circumferential direction of the concave groove portion 41 provided on the inner side cylindrical body 34 are set to correspond to each other so that the positions of both are overlapped as described above. However, in the present invention, it is also possible to provide the concave groove portions 41 of the inner side cylindrical body 34 at a forming pitch smaller than the forming pitch corresponding to the penetration holes 38 of the outer side cylindrical body 33.

Thereby, it is possible to form two or more micro pawl portions 23 in each engaging element.

Each concave groove portion 41 of the inner side cylindrical body 34 in the Embodiment 1 has a flat groove bottom surface and a pair of groove side wall surfaces disposed in parallel to oppose each other such that the cross section is rectangular. It should be noted that the concave groove portion 41 formed on the inner side cylindrical body 34 may be formed to have a substantially U-shaped cross section instead of the quadrangular cross section as described above.

In this case, the groove width (interval between a pair of groove side wall surfaces) of each concave groove portion 41 is set to be 0.01 mm or more and 0.10 mm or less, and preferably 0.03 mm or more and 0.08 mm or less. The groove depth (dimension from the outer peripheral surface of the inner side cylindrical body 34 to the groove bottom surface of the concave groove portion 41) is set to be 0.005 mm or less and 0.05 mm or less, preferably 0.005 mm or more and 0.03 mm or less, and further preferably 0.01 mm or more and 0.025 mm or less.

Since the groove width of the concave groove portion 41 is set to be 0.01 mm or more and the groove depth is set to 0.005 mm or more as described above, it is possible to smoothly flow the molten synthetic resin into each of the concave groove portions 41 of the inner side cylindrical body 34 via the penetration holes 38 of the inner side cylindrical body 33. Further, the molded primary molded body 1a can be stably drawn out from the concave groove portions 41. In addition, since the groove width of the concave groove portion 41 set to be 0.10 mm or less and the groove depth is set to be 0.05 mm or less, it is possible to stably form the rib portion 22 and the micro pawl portions 23 as above on each engaging element 20 of the molded surface fastener 1.

Regarding the positional relationship between the penetration hole 38 provided on the outer side cylindrical body 33 and the concave groove portion 41 provided on the inner side cylindrical body 34 in the Embodiment 1, as shown in FIGS. 9 and 10, the concave groove portions 41 of the inner side cylindrical body 34 cross the circular outer peripheral edges of the plurality of penetration holes 38 of the outer side cylindrical body 33. Thereby, the circular outer peripheral edge of each penetration hole 38 disposed on the inner peripheral surface of the outer side cylindrical body 33 has two groove overlapped portions 39a overlapping the concave groove portion 41 of the inner side cylindrical body 34 and two arc-shaped close contact parts 39b which are disposed between the two groove overlapped portions 39a and are in contact directly with the outer peripheral surface of the inner side cylindrical body 34.

Figure 11:
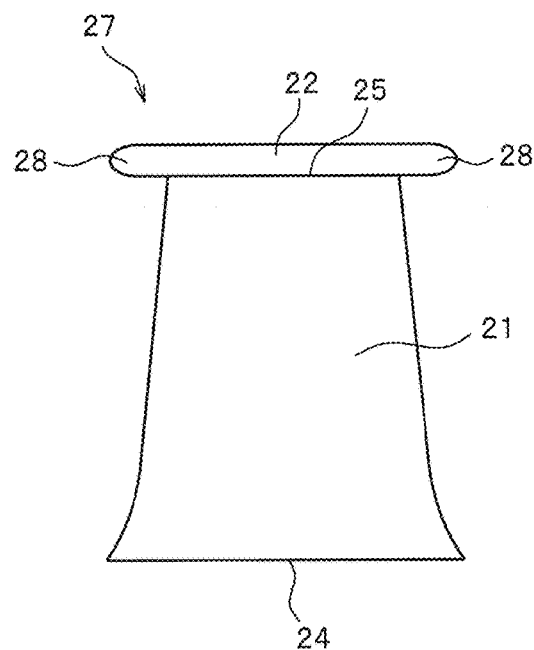
FIG. 11 is a front view of a provisional element only of a primary molded body obtained by the molding apparatus when viewed from a machine direction (MD).

Since the penetration holes 38 of the outer side cylindrical body 33 and the concave groove portions 41 of the inner side cylindrical body 34 are disposed as described above, when the primary molded body 1a is molded, as described later, it is possible to stably form a plurality of provisional elements 27 having the stem portion 21, the rib portion 22, and the protruded portion (provisional micro pawl portion) 28 on the base portion 10, as shown in FIG. 11. In this case, the groove width of the concave groove portion 41 is set to be ½ or less of the dimension of the penetration hole 38 in the M direction (the dimension of the diameter of the penetration hole 38 in the case of the Embodiment 1) of the inside peripheral surface of the outer side cylindrical body 33, preferably ⅓ or less, and further preferably ¼ or less.

A conveying apparatus (not shown) in the manufacturing apparatus 30 of the Embodiment 1 includes a conveying roller and the like, and has a structure capable of cooling the primary molded body 1a peeled off from the die wheel 32 by the pickup roller 37 while conveying horizontally in a state of the provisional elements 27 facing upward. In the present invention, the structure of this conveying apparatus is not limited, and installation of the conveying apparatus can be omitted.

In a case of manufacturing the molded surface fastener 1 using the manufacturing apparatus 30 having the molding apparatus 31 and the conveying apparatus as described above, first, a primary molding step for molding the primary molded body 1a by the molding apparatus 31 is conducted. In this primary molding step, the molten synthetic resin material is continuously extruded from the extrusion nozzle 36 toward the outer peripheral surface of the die wheel 32.

At this time, the die wheel 32 is drivingly rotated in one direction. Therefore, when the synthetic resin material is continuously extruded to the peripheral surface of the die wheel 32, thereby the base portion 10 of the molded surface fastener 1 is continuously molded between the extrusion nozzle 36 and the die wheel 32. In this case, the interval between the extrusion nozzle 36 and the die wheel 32 is adjusted to a size corresponding to a thickness dimension of the base portion 10 of the molded surface fastener 1 to be manufactured.

Simultaneously with molding the base portion 10, the plurality of provisional elements 27 as shown in FIG. 11 are molded integrally on the base portion 10 by the above mentioned outer side cylindrical body 33 and the inner side cylindrical body 34 of the die wheel 32, thereby the primary molded body 1a is produced.

Here, the primary molded body 1a (also referred to as a preformed body) molded by the molding apparatus 31 of the Embodiment 1 includes a thin plate-shaped base portion 10 and a plurality of provisional elements 27 standing on the upper surface of the base portion 10. The base portion 10 of the primary molded body 1a becomes the base portion 10 of the molded surface fastener 1 as it is. The provisional element 27 is a part to become the engaging element 20 of the molded surface fastener 1 by being partially deformed during conveyance by the conveying apparatus, as described later.

The provisional element 27 of the primary molded body 1a includes a frustum stem portion 21 standing on the base portion 10, a rib portion 22 protruding on the upper surface of the stem portion 21, and right and left protruded portions (provisional micro pawl portions) 28 continuously protruding from both end edges of the rib portion 22 substantially parallel to the upper surface of the base portion 10 so as to bulge an outside of the stem portion 21. In this case, the stem portion 21 and the rib portion 22 of the primary molded body 1a become the stem portion 21 and the rib portion 22 of the molded surface fastener 1 as they are.

The stem portion 21 of the primary molded body 1a is molded by filling the penetration hole 38 provided on the outer side cylindrical body 33 with the synthetic resin in the primary molding step. In the primary molding step, the rib portion 22 and the right and left protruded portions 28 of the primary molded body 1a are molded by flowing synthetic resin into the concave groove portion 41 provided on the inner side cylindrical body 34 from the penetration hole 38 of the outer side cylindrical body 33, and further entering a part which extends beyond the penetration hole 38 along the concave groove portion 41. In this case, the rib portion 22 and the right and left protruded portions 28 are formed along the C direction (CD).

The rib portion 22 and the right and left protruded portions 28 are molded from the concave groove portion 41 having a quadrangular cross section which is provided on the inner side cylindrical body 34. However, due to contraction when the rib portion 22 and the protruded portions 28 are cooled, the rib portion 22 and the protruded portions 28 are formed to be in a pole shape having a round substantially U-shaped cross section.

It should be noted that the right and left protruded portions 28 is molded not by filling the entirety of the concave groove portion 41 of the inner side cylindrical body 34 with the synthetic resin, but is formed such that the synthetic resin flowed into the concave groove portion 41 from the penetration hole 38 of the outer side cylindrical body 33 enters into a part (for example, at a distance of about 0.01 mm or more and 0.04 mm or less from the region of the penetration hole 38) of the concave groove portion 41 so as to slightly overflow from the forming region of the penetration hole 38 along the concave groove portion 41. The protruded portion 28 molded in the primary molding step is a part to be the micro pawl portion 23 of the molded surface fastener 1 by being deformed during the conveyance by the conveying apparatus (or when passed through between an upper side holding roller 37b and a lower side holding roller 37c in a case of the manufacturing apparatus 30a, as described later).

The primary molded body 1a as described above is obtained by half-rotating the molten synthetic resin extruded from the extrusion nozzle 36 while being supported on the outer peripheral surface of the die wheel 32 and being cooled. Thereafter, the primary molded body 1a is continuously peeled off from the outer peripheral surface of the die wheel 32 by the pickup roller 37. At this time, the protruded portion 28 of the primary molded body 1a is pulled out smoothly from the concave groove portion 41 of the inner side cylindrical body 34 and the penetration hole 38 of the outer side cylindrical body 33 while being deformed or elastically deformed according to the cooling condition of the protruded portion 28 or the like. Thereby, the primary molded body lain which the plurality of provisional elements 27 having the rib portion 22 which is protruded from the upper surface of the stem portion 21 and the protruded portions 28 which are protruded from the rib portion 22 in a direction crossing with (preferably orthogonal to) the standing direction of the stem portion 21 stand on the base portion 10 is obtained. In this case, when the primary molded body 1a is not sufficiently cured (solidified), for example, the protruded portions 28 of the primary molded body 1a are sometimes deformed into a shape which is curved or sloped upward so as to slope upward from the side end edges of the rib portion 22 toward the protruded tip ends, since the protruded portions 28 of the primary molded body 1a are drawn out while being in sliding contact with the inner peripheral surface of the penetration hole 38 of the outer side cylindrical body 33 from the concave groove portion 41 of the inner side cylindrical body 34.

Subsequently, the primary molded body 1a peeled off from the die wheel 32 is cooled while being horizontally conveyed by the conveying apparatus (not shown). At this time, since the provisional element 27 of the primary molded body 1a is not sufficiently cooled, the right and left protruded portions 28 of the provisional element 27 can be partially deformed and bent so as to hang downward due to its own weight by conveying the primary molded body 1a horizontally, and further conveying the primary molded body 1a while heating. Thereby, the micro pawl portions 23 protruding from the rib portion 22 toward the base portion 10 are formed, and a gap is formed between the micro pawl portion 23 and the stem portion 21. As a result, the molded surface fastener 1 of the Embodiment 1 shown in FIG. 1 is manufactured.

In the Embodiment 1, when the primary molded body 1a peeled off from the die wheel 32 is cooled to such an extent that the protruded portion 28 is not deformed, it is also possible to prompt the aforementioned bending deformation of the protruded portion 28 of the provisional element 27 by providing a heating part above the conveying apparatus or blowing hot air from above of the provisional element 27, or the like.

Thereafter, the manufactured molded surface fastener 1 elongated in the machine direction is conveyed toward a cutting part (not shown), cut to a predetermined length at the cutting part, and collected. Alternatively, the long molded surface fastener 1, as it is, is wound into a roll on a collecting roller or the like, and collected.

In the manufacturing method of the Embodiment 1 as above, since the secondary molding step included in the manufacturing method of Embodiment 4, described later, is not conducted, production rate and production efficiency of the molded surface fastener 1 can be improved. As a result, production cost of the molded surface fastener 1 can be reduced.

In the molded surface fastener 1 of the Embodiment 1 manufactured as described above, each engaging element 20 is provided with the right and left micro pawl portions 23 protruding from the rib portion 22 so as to hang obliquely downward. The engaging element 20 of the Embodiment 1 provided with the micro pawl portions 23 as above has a characteristic configuration completely different from those in a conventional J-shape, palm tree-shape, and mushroom-shape. The molded surface fastener 1 having the engaging element 20 in such a characteristic configuration has following characteristics which cannot be obtained from the conventional molded surface fasteners.

In the molded surface fastener 1 of the Embodiment 1, since the stem portion 21 of the engaging element 20 can be formed thick in a frustum shape, strength of the stem portion 21 can be increased. For this reason, even when the molded surface fastener 1 of the Embodiment 1 receives a large pressing force by being pressed strongly against the female surface fastener, for example, the stem portion 21 hardly bend, therefore, the shape of the engaging element 20 can be retained stably. As a result, it is possible to push the molded surface fastener 1 of the Embodiment 1 to a deeper position with respect to the female surface fastener, in other words, to insert each engaging element 20 of the molded surface fastener 1 deeply into near a root of the loop of the female surface fastener.

Furthermore, in the engaging element 20 of the Embodiment 1, the extremely small right and left micro pawl portions 23 protrude outward from the rib portion 22 and toward the base portion 10. Therefore, as compared with the conventional mushroom-shaped engaging element having the engaging head portion bulging in a disk shape at an upper end part, for example, the engaging element 20 of the Embodiment 1 can be easily inserted into a deeper position smoothly with respect to the loop of the female surface fastener. As a result, the molded surface fastener 1 of the Embodiment 1 catches the loop of the female surface fastener more easily.

Figure 4:
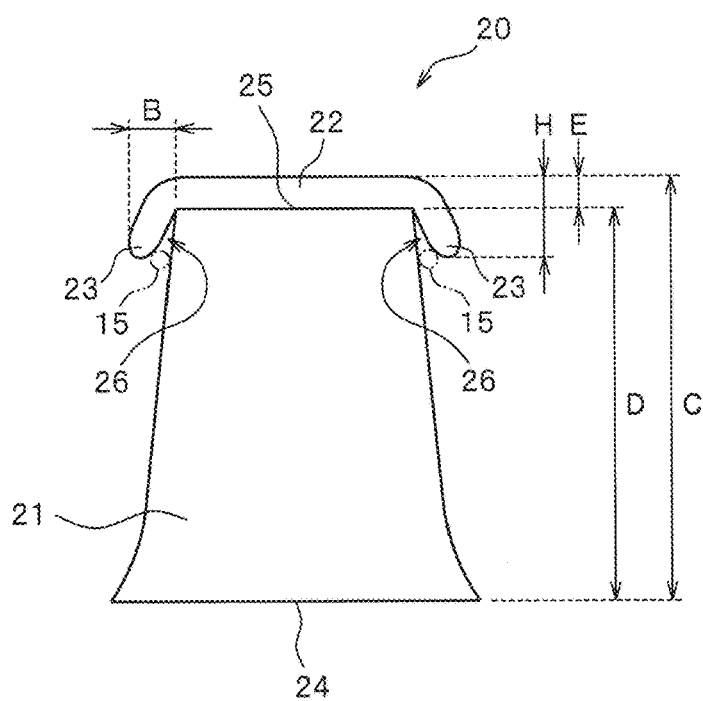
FIG. 4 is a front view of the engaging element only when viewed from a front and rear direction (machine direction: MD) of the molded surface fastener.
Figure 5:
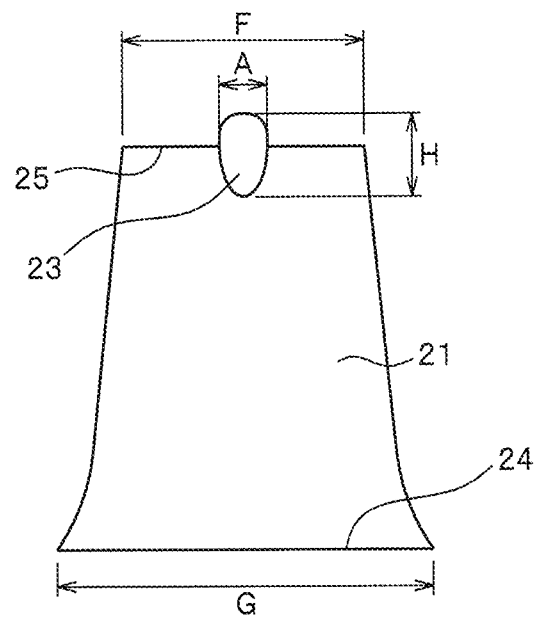
FIG. 5 is a side view of the engaging element only when viewed from a right and left direction (crossing direction: CD) of the molded surface fastener.

Further, in this case, the loop 15 of the female surface fastener can be stably engaged with the hanging micro pawl portions 23 of the engaging element 20 as shown with the imaginary line in FIG. 4 (the loop 15 can be held between the stem portion 21 and the micro pawl portions 23 stably).

Further, it can be expected that the loop 15 hooked by the hanging micro pawl portions 23 hardly comes off from the engaging element 20.

Therefore, the molded surface fastener 1 of the Embodiment 1 can have a high peel strength with respect to the female surface fastener. Here, the peel strength means an engaging strength when the molded surface fastener 1 and the female surface fastener are pulled to separate relatively in a height direction of the molded surface fastener 1 in a state when the female surface fastener is attached to the molded surface fastener 1. In the engaging element 20 of the Embodiment 1, the loop 15 is not engaged at a portion other than the micro pawl portions 23.

In this case, the protrusion length B of the micro pawl portion 23 in a plan view of the engaging element 20 is preferably set to be 50% or more and 300% or less of a cross-sectional diameter of the loop engaged with the molded surface fastener 1, and particularly 80% or more and 250% or less. Further, the size J of the gap 26 formed between the micro pawl portion 23 and the outer peripheral side surface of the stem portion 21 is preferably set to be 45% or more and 290% or less of a cross-sectional diameter of the loop engaged with the molded surface fastener 1, and particularly 70% or more and 240% or less.

Furthermore, in the molded surface fastener 1 of the Embodiment 1, a strength of the stem portion 21 is increased by forming the stem portion 21 thick in a frustum shape. As a result, a shear strength of the molded surface fastener 1 with respect to the female surface fastener can also be effectively increased. Here, the shear strength refers to an engaging strength of the molded surface fastener 1 when the molded surface fastener 1 and the female surface fastener are pulled relatively so as to shift in a length direction and a width direction of the molded surface fastener 1 in a state that the female surface fastener is attached to the molded surface fastener 1.

In particular, in the molded surface fastener 1 of the Embodiment 1, the engaging elements 20 can be disposed at higher density than the conventional ones as described above. Therefore, in the Embodiment 1, it is possible to choose the forming density of the engaging elements 20 from a wider range than the conventional male molded surface fasteners (enlarge a range of choice of the forming density). That is, the molded surface fastener 1 of the Embodiment 1 can adopt a more optimum forming density with respect to the female surface fastener to be combined. Accordingly, it is expected that the molded surface fastener 1 of the Embodiment 1 can be favorably combined with the female surface fastener in which loops are formed at a high density and which is incompatible with the conventional male molded surface fasteners, for example.

In addition, in the molded surface fastener 1 of the Embodiment 1, the upper surface of the engaging element 20 is formed such that the flat and smooth circular upper end surface 21a of the stem portion 21 is exposed with a large area. Therefore, when the molded surface fastener 1 of the Embodiment 1 is touched from the upper surface side to be an engaging surface, the smooth upper surface of the engaging element 20 is easily touched widely to the skin.

In this case, the size of the rib portion 22 and the micro pawl portions 23 of the engaging element 20 is formed to be small, and the upper surface of the rib portion 22 and the outer surface of the micro pawl portions 23 are formed as curved surfaces. Therefore, when the engaging element 20 of the Embodiment 1 is touched from the upper side, the feeling of discomfort given to the texture of the rib portion 22 and the micro pawl portions 23 of the engaging element 20 can be reduced. Therefore, in the molded surface fastener 1 of the Embodiment 1, it is possible to stably obtain a better texture and touch comfort than in the conventional molded surface fasteners having a J-shaped or palm tree-shaped engaging element.

As described above, the molded surface fastener 1 of the Embodiment 1 is provided with a high peel strength with respect to the female surface fastener similar to a conventional J-shaped or palm tree-shaped engaging element. At the same time, pleasant texture as the conventional mushroom-shaped engaging element can be stably obtained. Furthermore, the molded surface fastener 1 of the Embodiment 1 is expected to have a new property that the compatibility with the female surface fastener on which loops are formed at a high density is improved.

As described above, the molded surface fastener 1 of the Embodiment 1 which is high in a peel strength and a shear strength and has pleasant texture can be favorably used as, for example, disposable diapers, diaper covers for infant, supporters for protecting the joints of limbs, corsets for waist, gloves and the like which are wearable to the body.

As described above, the molded surface fastener 1 of the Embodiment 1 is manufactured such that the primary molded body 1a molded by using the die wheel 32 of the manufacturing apparatus 30 shown in FIG. 7 is peeled off from the die wheel 32, afterwards, the protruded portion 28 of the provisional element 27 in the primary molded body 1a is partially bent and deformed downward by its own weight or by blowing hot air from above.

Figure 12:
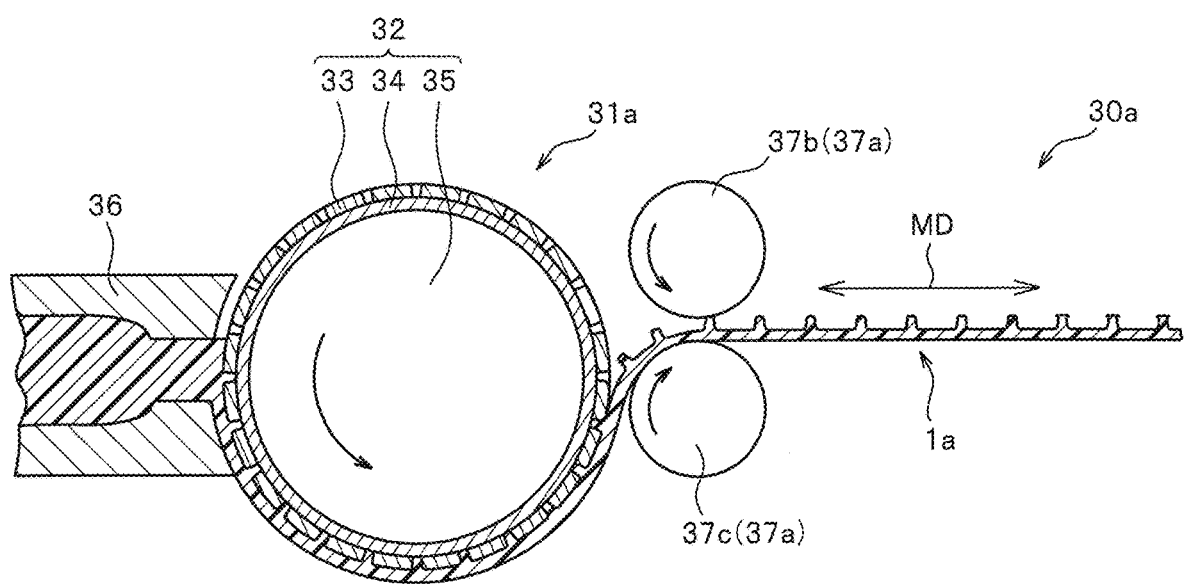
FIG. 12 is a schematic view schematically illustrating another molding apparatus of the molded surface fastener in Embodiment 1.

However, in the Embodiment 1, it is also possible to manufacture the molded surface fastener 1 of the Embodiment 1 stably such that the protruded portion 28 of the provisional element 27 in the primary molded body 1a is intentionally bent and deformed by using another manufacturing apparatus 30a according to a modification example as shown in FIG. 12, for example.

Here, the manufacturing apparatus 30a shown in FIG. 12 includes a molding apparatus 31a for conducting the primary molding step and a conveying apparatus (not shown) for cooling the primary molded body 1a molded in the primary molding step while conveying. In this case, it is also possible to omit the installation of the conveying apparatus.

This molding apparatus 31a includes a die wheel 32 drivingly rotating in one direction (counterclockwise direction in the drawings), an extrusion nozzle 36 which is disposed to face the peripheral surface of the die wheel 32 and extrude continuously the molten synthetic resin material, and pickup rollers 37a disposed on the downstream side of the extrusion nozzle 36 in the rotation direction of the die wheel 32. In this case, the die wheel 32 and the extrusion nozzle 36 are formed in the same manner as the die wheel 32 and the extrusion nozzle 36 of the molding apparatus 31 shown in FIG. 7.

The pickup rollers 37a of the molding apparatus 31a include a pair of upper side holding roller 37b and a lower side holding roller 37c for holding and pulling the primary molded body 1a molded at the peripheral surface portion of the die wheel 32 from upper and lower sides. In addition, a surface layer (not shown) made of an elastomer such as polyurethane elastomer is provided on the outer peripheral surface part of the upper side holding roller 37b in contact with the primary molded body 1a and on the outer peripheral surface part of the lower side holding roller 37c in contact with the primary molded body 1a.

The upper side holding roller 37b and the lower side holding roller 37c are disposed to face each other with a predetermined interval. The upper side holding roller 37b and the lower side holding roller 37*c* rotate in a predetermined direction at a predetermined speed respectively, thereby the primary molded body 1*a* can be conveyed smoothly to the downstream side while continuously being peeled off from the die wheel 32.

In a case of manufacturing the molded surface fastener 1 using such a manufacturing apparatus 30*a*, the above described primary molded body 1*a* is molded at the peripheral surface part of the die wheel 32 by continuously extruding the molten synthetic resin material from the extrusion nozzle 36 toward the outer peripheral surface of the die wheel 32. The molded primary molded body 1*a* is cooled while being supported on the outer peripheral surface of the rotating die wheel 32 and thereafter, continuously peeled off from the outer peripheral surface of the die wheel 32 by the pickup rollers 37*a*. At this time, when the primary molded body 1*a* is not sufficiently cooled, the protruded portion 28 of the provisional element 27 in the primary molded body 1*a* is deformed in a curved or sloped shape upward so as to slope upward from the side end edges of the rib portion 22 toward the protruded tip ends.

The primary molded body 1*a* peeled off from the die wheel 32 is held between the upper side holding roller 37*b* and the lower side holding roller 37*c* disposed to be apart at a predetermined interval from each other of the pickup rollers 37*a* immediately thereafter. As a result, since the protruded portion 28 of the provisional element 27 which is curved or sloped upward is pressed from above by the upper side holding roller 37*b*, as described above, the protruded portion 28 is forcibly (intentionally) deformed plastically so as to partially bend downward. As a result, the protruded portion 28 of the provisional element 27 can be curved or sloped downward so as to slope downward from the side end edges of the rib portion 22 toward the base portion 10 (or can be protruded in a horizontal direction substantially parallel to the upper surface of the base portion).

Further, in this case, the molded surface fastener 1 obtained by being passed between the upper side holding roller 37*b* and the lower side holding roller 37*c* is cooled while being horizontally conveyed by a conveying apparatus (not shown). At this time, it is also possible to further prompt the right and left micro pawl portions 23 of the engaging element 20 to be bent and deformed by its own weight and/or blowing hot air from above. Therefore, even when the protruded portion 28 of the provisional element 27 which has passed between the upper side holding roller 37*b* and the lower side holding roller 37*c* protrudes in the horizontal direction substantially parallel to the upper surface of the base portion 10 as described above, for example, the protruded portion 28 of the provisional element 27 can be curved or sloped stably downward from the side end edges of the rib portion 22.

Therefore, in the Embodiment 1, it is possible to more stably and smoothly manufacture the molded surface fastener 1 of the Embodiment 1 shown in FIG. 1 by using the manufacturing apparatus 30*a* according to the modification example shown in FIG. 12.

In the Embodiment 1 as described above, the primary molded body 1*a* on which the plurality of provisional elements 27 shown in FIG. 11 stand on the base portion 10 is molded, and thereafter, the protruded portion 28 of the provisional element 27 is bent and deformed downward to manufacture the molded surface fastener 1 to be a product. However, in the present invention, it is also possible that the protruded portion 28 is formed to be protruded substantially parallel to the upper surface of the base portion 10, after the primary molded body 1*a* provided with the plurality of provisional elements 27 as shown in FIG. 11 standing on the base portion 10 is sufficiently cooled at the peripheral surface part of the die wheel 32, for example, the primary molded body 1*a* is peeled off from the die wheel 32 while being elastically deformed. Thereby, it is possible to manufacture a molded surface fastener having the provisional element 27 in FIG. 11 as an engaging element. That is, it is also possible to provide as it is the primary molded body 1*a* obtained at the peripheral surface part of the die wheel 32 in the primary molding step as above as a molded surface fastener.

Furthermore, when the primary molded body 1*a* is peeled off from the die wheel 32, the right and left protruded portions 28 of the provisional element 27 are sometimes curved or sloped so as to slope upward from the side end edges of the rib portion 22, as described above. In this case, it is possible to appropriately deform the protruded portion 28 sloped upward from the rib portion 22 and to direct the protruding direction of the protruded portion 28 to a direction substantially parallel to the upper surface of the base portion 10 by its own weight and/or by blowing hot air from above, or by passing the primary molded body 1*a* between an upper and lower pair of the upper side holding roller 37*b* and the lower side holding roller 37*c* of the pickup rollers 37*a* as shown in FIG. 12 while conveying the primary molded body 1*a* with a conveying apparatus (not shown). As above, it is also possible to manufacture a molded surface fastener having the provisional element 27 of FIG. 11 as an engaging element.

In this case, each engaging element of the molded surface fastener to be manufactured has the two protruded portions 28 of the provisional element 27 in FIG. 11 as the micro pawl portions. Therefore, the micro pawl portions protrude outward from the upper end outer peripheral edge of the stem portion in a plan view of the engaging element, in parallel with the upper surface of the base portion (or in slightly sloped directions toward the base portion with respect to the upper surface of the base portion). Further, the pawl width dimension of the micro pawl portions is set to be ½ or less of the diameter of the circular upper end surface of the stem portion, preferably ⅓ or less, and further preferably ¼ or less.

Therefore, the molded surface fastener having such a provisional element 27 as an engaging element has a high peel strength by the micro pawl portion (protruded portion 28) with respect to the female surface fastener, and also can stably obtain the pleasant texture and the touch comfort same as the Embodiment 1. Further, in the present invention, the primary molded body molded in the primary molding step can be provided as it is as a molded surface fastener in not only this Embodiment 1 but also in the case of Embodiment 2 and Embodiment 3, described later.

Embodiment 2

Figure 13:
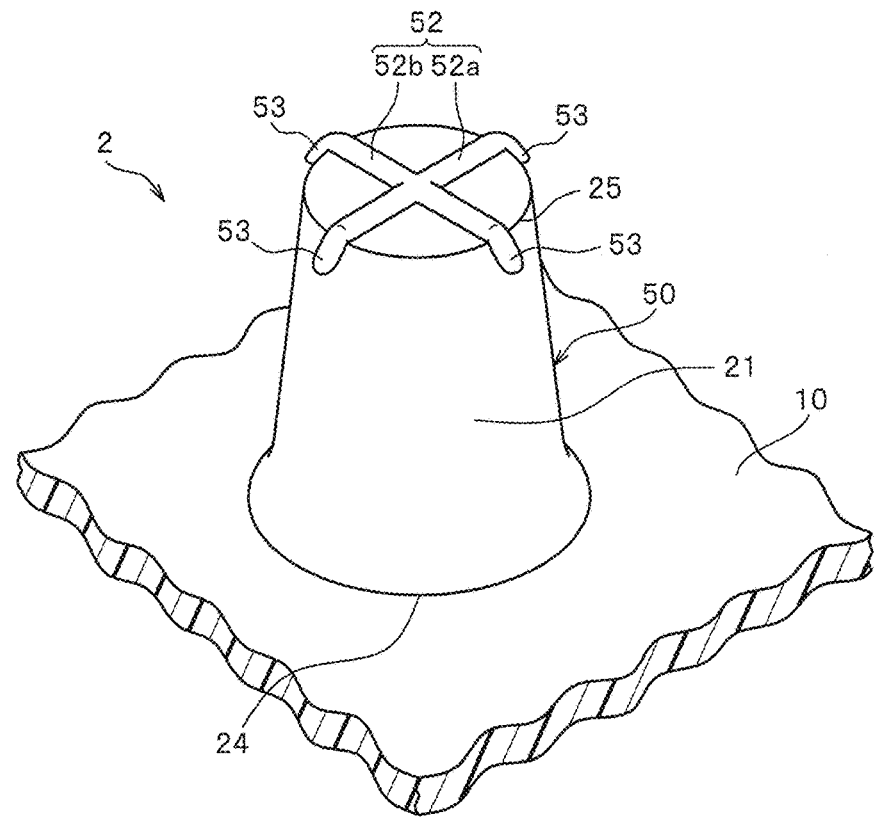
FIG. 13 is a perspective view illustrating an engaging element of a molded surface fastener according to Embodiment 2 of the present invention.
Figure 14:
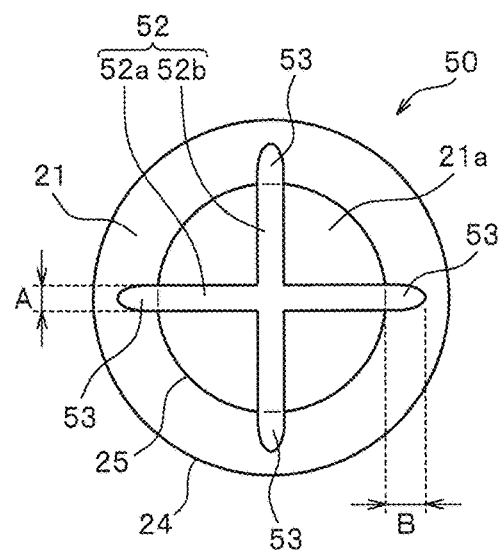
FIG. 14 is a plan view illustrating the engaging element only.
Figure 15:
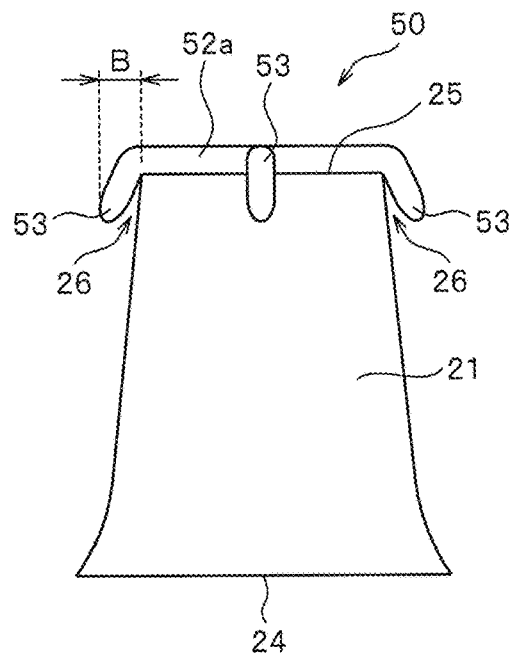
FIG. 15 is a front view of the engaging element only when viewed from a front and rear direction (machine direction: MD) of the molded surface fastener.

FIGS. 13 to 15 are schematic views of the engaging element provided in the molded surface fastener of the Embodiment 2 as viewed from various directions.

The molded surface fastener 2 of the Embodiment 2 is formed such that the configuration of the rib portions 52 and the micro pawl portions 53 of the engaging element 50 is different from those of the molded surface fastener 1 of the Embodiment 1 as described above. In the Embodiment 2 and each embodiment and each modification example described later, the configuration different from the molded surface fastener 1 according to the above-described Embodiment 1 will be mainly described, and parts or members having substantially the same configuration as the molded surface fastener 1 according to the above-mentioned Embodiment 1 are expressed by the same reference numerals, and the description thereof will be omitted.

In the molded surface fastener 2 of the Embodiment 2, a plurality of engaging elements 50 are disposed on the upper surface of the base portion 10 so as to be aligned along a front and rear direction (MD) and a right and left direction (CD). Each engaging element 50 includes a stem portion 21 standing on the base portion 10, rib portions 52 protruded from an upper end surface 21a of the stem portion 21 along the front and rear direction (MD) and the right and left direction (CD), and four micro pawl portions 53 protruding outward from each end edge of the rib portions 52, respectively.

The stem portion 21 of the Embodiment 2 has the same configuration as the stem portion 21 of the above described Embodiment 1. The rib portions 52 of the Embodiment 2 include a first rib portion 52a bulging upward from the upper end surface 21a of the stem portion 21 along the right and left direction and a second rib portion 52b bulging upward from the upper end surface 21a of the stem portion 21 along the front and rear direction.

These first rib portion 52a and the second rib portion 52b are disposed along a diameter of the circular upper end surface 21a of the stem portion 21 and are crossed mutually in a cross shape at a center part of the circular upper end surface 21a of the stem portion 21. The upper surfaces of the first rib portion 52a and the second rib portion 52b are formed to be curved surfaces curved upward in a convex shape so as to be rounded.

In the present invention, a rib width dimension of the first rib portion 52a and the second rib portion 52b can be arbitrarily changed. In this case, the rib width dimension of the first rib portion 52a and the second rib portion 52b are set to be 1/10 or more and 1/2 or less of the diameter of the circular upper end surface 21a in the stem portion 21, preferably 1/8 or more 1/3 or less, and further preferably 1/6 or more and 1/4 or less as in the case of the Embodiment 1.

In a plan view of the engaging element 50 (see FIG. 14), the micro pawl portions 53 of the Embodiment 2 are protruded outwardly from both end edges of each of the first rib portion 52a and the second rib portion 52b along a radial direction of the circular upper end surface 21a of the stem portion 21. In this case, in a plan view of the engaging element 50, the four micro pawl portions 53 are regularly disposed at positions of 0°, 90°, 180° and 270° with reference to the center of the circular upper end surface 21a of the stem portion 21.

The two micro pawl portions 53 protruding in the right and left direction are formed point-symmetrically each other based on the center of the circular upper end surface 21a of the stem portion 21 in a plan view of the engaging element 50. The two micro pawl portions 53 protruding in the front and rear direction are also formed point-symmetrically each other based on the center of the circular upper end surface 21a of the stem portion 21 in a plan view of the engaging element 50.

Further, the front, rear, right and left micro pawl portions 53 protrude from the respective end edges of the first rib portion 52a and the second rib portion 52b so as to slope downward to the base portion 10 such that pawl tip ends hang downward. As a result, a gap 26 is formed between the micro pawl portion 53 and the outer peripheral side surface of the stem portion 21.

Each of the micro pawl portions 53 of the Embodiment 2 has a round shape as a whole and becomes thinner toward the pawl tip end. Further, in a plan view of the engaging element 50, each micro pawl portion 53 is formed within a donut-shaped region between the upper end outer peripheral edge 25 on the upper surface of the stem portion 21 and the circular outer peripheral edge 24 at the base end of the stem portion 21.

In this case, a pawl width dimension A of the micro pawl portion 53 is set to be 1/10 or more and 1/2 or less of the diameter of the circular upper end surface 21a of the stem portion 21 (in particular, the diameter along the front and rear direction), preferably 1/8 or more and 1/3 or less, and further preferably 1/6 or more and 1/4 or less as in the case of the Embodiment 1.

A protrusion length B of the micro pawl portions 53 in a plan view of the engaging element 50 is set to be 1/2 or less of the diameter of the circular upper end surface 21a of the stem portion 21, preferably 1/3 or less, and further preferably 1/4 or less. In the Embodiment 2, specific range of the size of each portion of the engaging element 50 and specific range of the forming density are the same as in the Embodiment 1.

Figure 16:
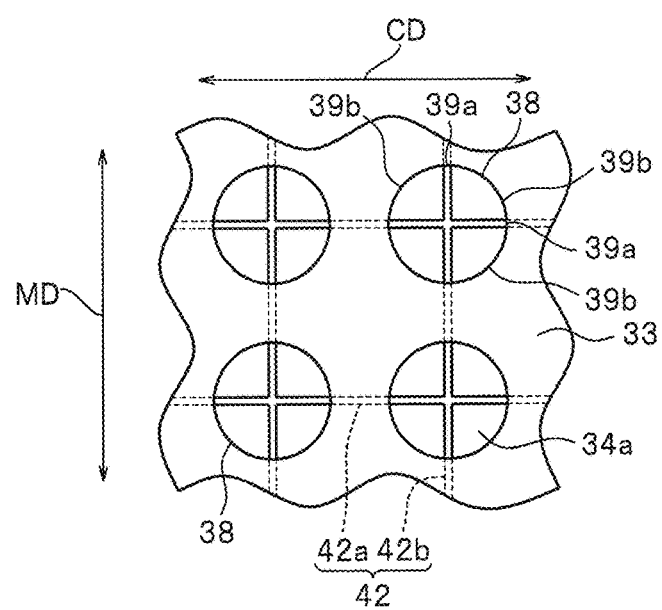
FIG. 16 is a schematic view of a main part illustrating a positional relationship between a penetration hole formed on an outer side cylindrical body and a concave groove portion provided on an inner side cylindrical body of the molding apparatus according to the Embodiment 2.

The molded surface fastener 2 of the Embodiment 2 having the engaging element 50 protrudingly provided with four micro pawl portions 53 is manufactured by using the manufacturing apparatus 30 as shown in FIG. 7 as in the Embodiment 1. Alternatively, it is also possible to manufacture the molded surface fastener 2 of the Embodiment 2 by using the manufacturing apparatus 30a as shown in FIG. 12. In the Embodiment 2, although the outer side cylindrical body 33 of the die wheel 32 in the manufacturing apparatus 30 or the manufacturing apparatus 30a is formed in the same manner as in the Embodiment 1, the inner side cylindrical body 34a of the die wheel 32 has a different structure from the inner side cylindrical body 34 used in the above-described Embodiment 1 in order to provide the four micro pawl portions 53 in the engaging element 50 as shown in FIG. 16.

Specifically, the inner side cylindrical body (inner sleeve) 34a used in the Embodiment 2 includes a plurality of concave groove portions 42 formed on the outer peripheral surface. In this case, the concave groove portion 42 of the Embodiment 2 includes a plurality of first concave groove portions 42a along the C direction and a plurality of second concave groove portions 42b along the circumferential direction of the cylinder to be the M direction.

The first concave groove portion 42a in the C direction and the second concave groove portion 42b in the M direction respectively overlap with the diameters of the penetration hole 38 formed on the outer side cylindrical body 33. In this case, the first concave groove portion 42a and the second concave groove portion 42b are formed at a predetermined pitch so as to be orthogonal to each other at the center position of each penetration hole 38.

Therefore, a circular outer peripheral edge of each penetration hole 38 disposed on the inner peripheral surface of the outer side cylindrical body 33 includes four groove overlapped parts 39a overlapping with the first concave groove portion 42a and the second concave groove portion 42b of the inner side cylindrical body 34a and four arc-shaped close contact parts 39b which are in direct contact with the outer peripheral surface of the inner side cylindrical body 34a.

In the Embodiment 2, the primary molded body is molded by conducting the primary molding step using the molding apparatus 31 having the inner side cylindrical body 34a as described above. The primary molded body of the Embodiment 2 is provided with a plurality of provisional elements standing on the base portion 10 and having a stem portion 21, a cross-shaped rib portion 52 protruding on the upper end surface 21a of the stem portion 21, and four protruded portions protruding in parallel with the rib portion 52 so as to bulge from each end edge of the rib portion 52 toward outside of the stem portion 21.

When the manufacturing apparatus 30 is used, the primary molded body of the Embodiment 2 is cooled while being horizontally conveyed by a conveying apparatus (not shown) as in the above-mentioned Embodiment 1. At this time, the front, rear, right and left protruded portions of the provisional element are partially bent and deformed so as to hang downward by its own weight and/or blowing hot air from above, for example. Thereby, the molded surface fastener 2 of the Embodiment 2 provided with the micro pawl portions 53 protruding from the rib portions 52 toward the base portion 10 is manufactured.

On the other hand, in a case of using the manufacturing apparatus 30a, the primary molded body of the Embodiment 2 peeled off from the outer peripheral surface of the die wheel 32 by the upper side holding roller 37b and the lower side holding roller 37c of the pickup rollers 37a passes through between the upper side holding roller 37b and the lower side holding roller 37c. At this time, since the front, rear, right and left protruded portions of the provisional element of the primary molded body are pressed from above by the upper side holding roller 37b, they are forcibly bent and deformed to hang downward. The molded surface fastener 2 of the Embodiment 2 having the micro pawl portions 53 protruding from the rib portion 52 toward the base portion 10 is also manufactured by the above.

As described above, the molded surface fastener 2 of the Embodiment 2 manufactured using the manufacturing apparatus 30 or the manufacturing apparatus 30a has four micro pawl portions 53 provided in each engaging element, more than the ones in the molded surface fastener 1 of the above-mentioned Embodiment 1. Therefore, in the molded surface fastener 2 of the Embodiment 2, higher peel strength than that of the molded surface fastener 1 of the above described Embodiment 1 can be obtained.

In the molded surface fastener 2 of the Embodiment 2, the upper end surface 21a of the stem portion 21 in the engaging element 50 is formed flat. The first rib portion 52a, the second rib portion 52b, and the four micro pawl portions 53 of the engaging element 50 are very small, and the upper surfaces of the first rib portion 52a and the second rib portion 52b and the outer surfaces of the four micro pawl portions 53 are formed to be curved surfaces. Therefore, also with the molded surface fastener 2 of the Embodiment 2, the pleasant texture and the touch comfort can be stably obtained.

Embodiment 3

Figure 17:
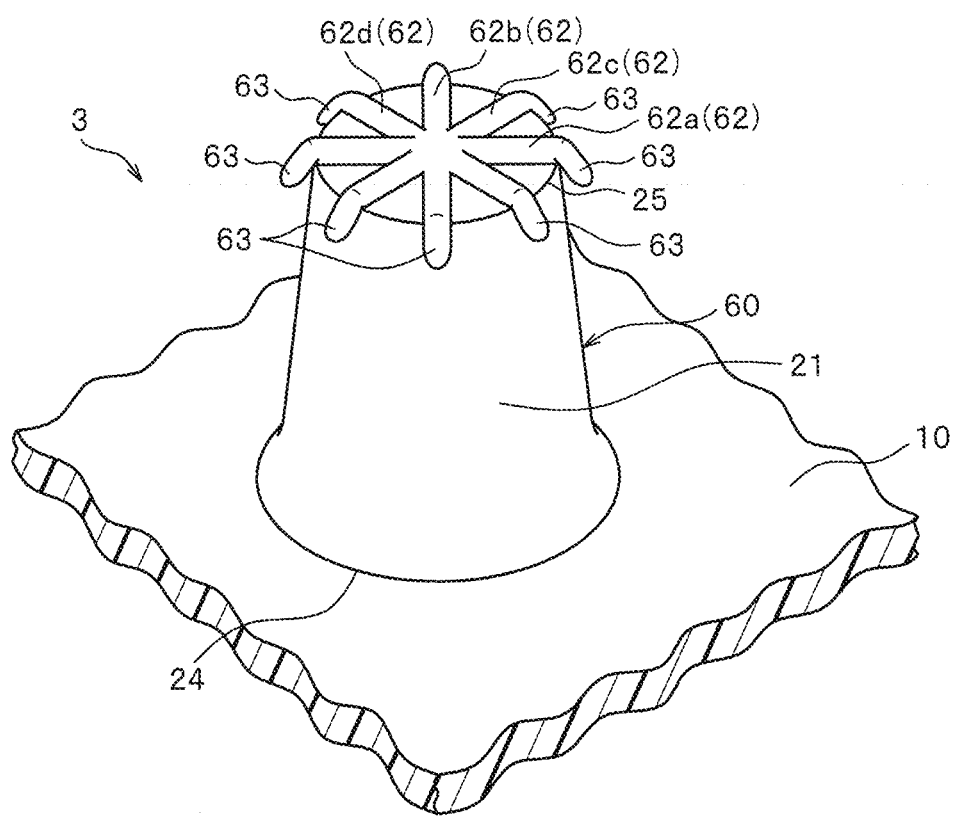
FIG. 17 is a perspective view illustrating an engaging element of a molded surface fastener according to Embodiment 3 of the present invention.
Figure 18:
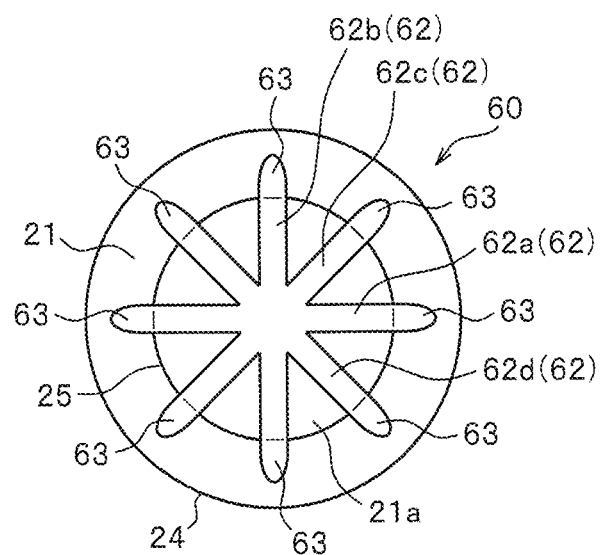
FIG. 18 is a plan view illustrating the engaging element only.

FIG. 17 is a perspective view illustrating an engaging element of a molded surface fastener according to Embodiment 3. FIG. 18 is a plan view of the engaging element.

In the molded surface fastener 3 of the Embodiment 3, a plurality of engaging elements 60 are disposed on an upper surface of the base portion 10 so as to be aligned along a front and rear direction (MD) and a right and left direction (CD). Each engaging element 60 includes a stem portion 21 standing on the base portion 10, rib portions 62 protruding on an upper end surface 21a of the stem portion 21, and eight micro pawl portions 63 protruding outward from each end edge of the rib portions 62.

The rib portions 62 of the Embodiment 3 include a first rib portion 62a bulging upward from the upper end surface 21a of the stem portion 21 along the right and left direction, a second rib portion 62b bulging upward from the upper end surface 21a of the stem portion 21 along the front and rear direction, and a third rib portion 62c and a fourth rib portion 62d bulging upward from the upper end surface 21a of the stem portion 21 so as to form an inclination angle of 45° with respect to the first rib portion 62a and the second rib portion 62b.

The first rib portion 62a to the fourth rib portion 62d are disposed along a diameter of the circular upper end surface 21a of the stem portion 21 and cross each other at a center part of the circular upper end surface 21a of the stem portion 21. In this case, the first rib portion 62a and the second rib portion 62b cross each other in a cross shape, and the third rib portion 62c and the fourth rib portion 62d cross each other in a cross shape. Therefore, the first rib portion 62a to the fourth rib portion 62d extend in eight directions from the center part of the circular upper end surface 21a of the stem portion 21.

In this case, upper surfaces of the first rib portion 62a to the fourth rib portion 62d are formed into a curved surface curving upward in a convex shape so as to be rounded. In addition, a rib width dimension of the first rib portion 62a to the fourth rib portion 62d can be arbitrarily set in the same range as in the aforementioned Embodiment 1.

In a plan view of the engaging element 60, the micro pawl portions 63 of the Embodiment 3 are protruded outward along a radial direction of the circular upper end surface 21a of the stem portion 21 from both end edges of the respective first rib portion 62a to the fourth rib portion 62d. That is, the eight micro pawl portions 63 of the Embodiment 3 are disposed regularly at predetermined intervals such that an angle of 45° is formed with respect to the adjacent micro pawl portions 63 with reference to the center of the circular upper end surface 21a of the stem portion 21.

Further, each micro pawl portion 63 protrudes in a form of being sloped from the each end edge of the first rib portion 62a to the fourth rib portion 62d toward the base portion 10 such that a pawl tip end hangs downward. Thereby, a gap is formed between the micro pawl portion 63 and the outer peripheral side surface of the stem portion 21, respectively. Further, in a plan view of the engaging element 60, each micro pawl portion 63 is formed within a donut-shaped region between the circular upper end outer peripheral edge 25 on the upper surface of the stem portion 21 and the circular outer peripheral edge 24 at the base end of the stem portion 21. Each micro pawl portion 63 of the Embodiment 3 has the same configuration and size as those of the micro pawl portions 23 of the above-described Embodiment 2.

Figure 19:
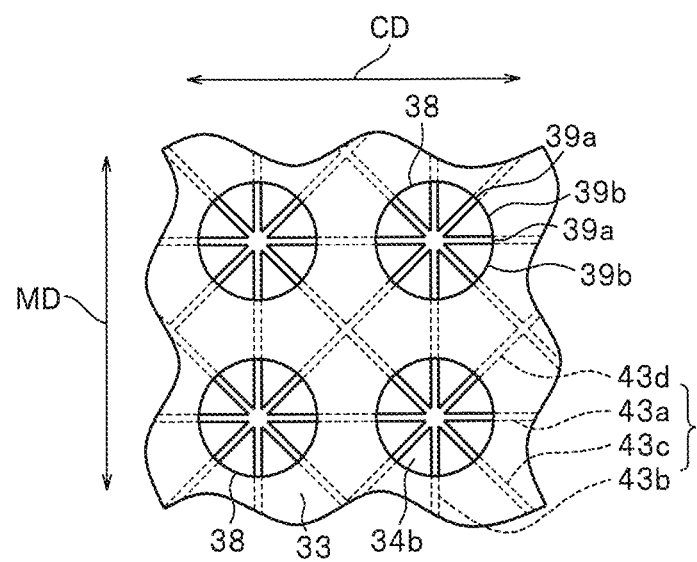
FIG. 19 is a schematic view of a main part illustrating a positional relationship between a penetration hole formed on an outer side cylindrical body and a concave groove portion provided on an inner side cylindrical body of the molding apparatus according to the Embodiment 3.

The molded surface fastener 3 of the Embodiment 3 including the engaging element 60 provided with the eight micro pawl portions 63 is manufactured using a manufacturing apparatus 30 shown in FIG. 7 or a manufacturing apparatus 30a shown in FIG. 12 as in the case of the aforementioned Embodiment 1. In the Embodiment 3, for providing the eight micro pawl portions 63 to the engaging element 60, an inner side cylindrical body 34b of a die wheel 32 is different from the inner side cylindrical body 34 used in the above-described Embodiment 1, as shown in FIG. 19.

That is, as a concave groove portion 43, a plurality of linear first concave groove portions 43a disposed along the C direction, a plurality of second concave groove portions 43b disposed along the circumferential direction of the cylinder to be the M direction, and a plurality of third concave groove portions 43c and fourth concave groove portions 43d disposed at an inclination angle of 45° with respect to the first concave groove portion 43a and the second concave groove portion 43b are concaved on the outer peripheral surface of the inner side cylindrical body 34b of the Embodiment 3.

In this case, the first concave groove portion 43a to the fourth concave groove portion 43d are formed at predetermined pitches to overlap with a diameter of a penetration hole 38 formed on the outer side cylindrical body 33, and to cross each other at center positions of each penetration hole 38.

Therefore, the circular outer peripheral edge of each penetration hole 38 disposed on the inner peripheral surface of the outer side cylindrical body 33 includes a groove overlapped portion 39a overlapping with the first concave groove portion 43a to the fourth concave groove portion 43d of the inner side cylindrical body 34b and an arc-shaped close contact portion 39b which is in direct contact with the outer peripheral surface of the inner side cylindrical body 34b.

In the Embodiment 3, a primary molded body is molded by conducting a primary molding step using the molding apparatus 31 or the molding apparatus 31a provided with the inner side cylindrical body 34b as described above. In the primary molded body of the Embodiment 3, a plurality of provisional elements in which a stem portion 21, rib portions 62 protruding on the upper end surface 21a of the stem portion 21 and extending in eight directions from a center part of the upper end surface 21a, and eight protruded portions which is protruded in parallel with the rib portions 62 so as to bulge toward outside of the stem portion from each end edge of the rib portions 62 stand on the base portion 10.

In the Embodiment 3, as in the case of aforementioned Embodiments 1 and 2, each protruded portion of the primary molded body is partially deformed so as to hang downward after the primary molding step. Thereby, the molded surface fastener 3 of the Embodiment 3 is manufactured.

In the molded surface fastener 3 of the Embodiment 3, the number of the micro pawl portions 63 provided on each engaging element 60 is eight, therefore, a higher peel strength can be easily obtained than the molded surface fastener 1 of the Embodiment 1 and the molded surface fastener 2 of the Embodiment 2 as mentioned above. Also in the molded surface fastener 3 of the Embodiment 3, it is possible to stably obtain a pleasant texture and the touch comfort as in the case of the above described Embodiment 1 and Embodiment 2.

Embodiment 4

Figure 20:
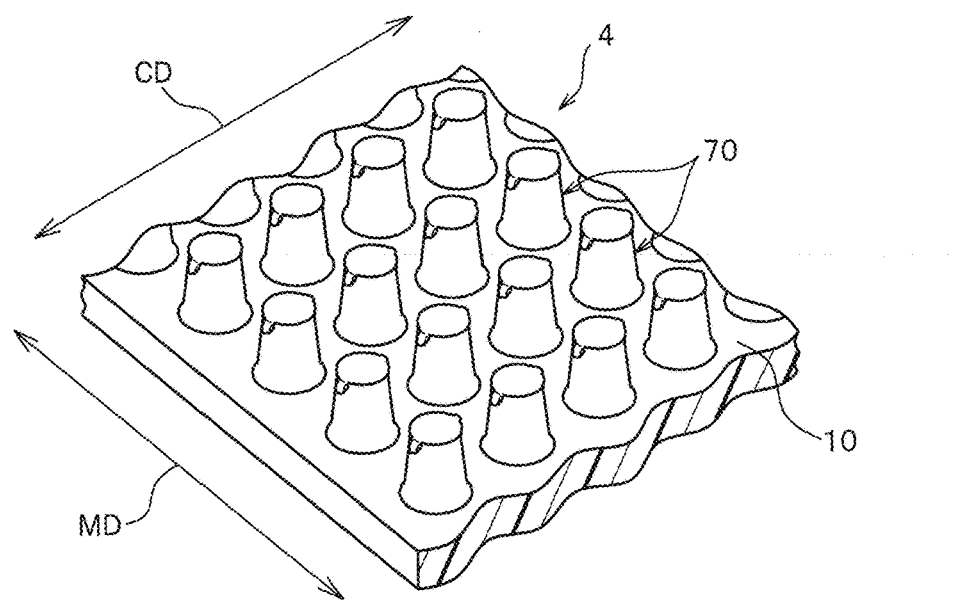
FIG. 20 is a perspective view illustrating a molded surface fastener according to Embodiment 4 of the present invention.
Figure 25:
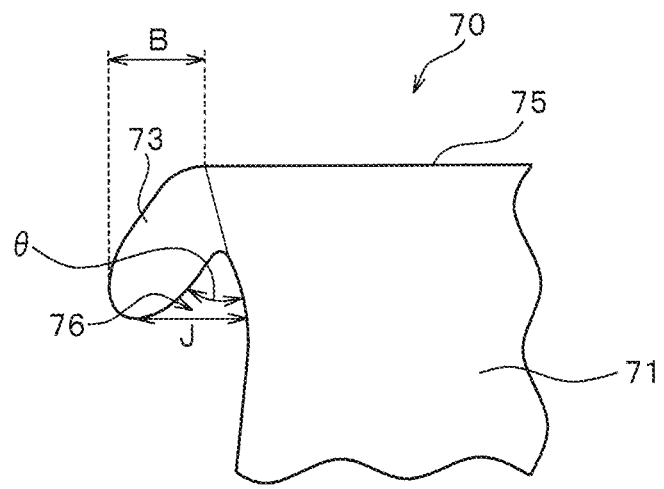
FIG. 25 is an enlarged front view enlarging a micro pawl portion of the engaging element.

FIG. 20 is a perspective view illustrating a molded surface fastener according to Embodiment 4. FIGS. 21 to 24 are views illustrating an engaging element of the molded surface fastener viewed from various directions. FIG. 25 is an enlarged view illustrating an enlarged micro pawl portion disposed on the engaging element.

In the molded surface fastener 4 of the Embodiment 4, a plurality of engaging elements 70 are disposed on an upper surface of a base portion 10 so as to be aligned along a front and rear direction (MD) and a right and left direction (CD). Each engaging element 70 includes a stem portion 71 standing on the base portion 10 and two micro pawl portions 73 protruding toward right and left from an outer peripheral side surface of the stem portion 71. The rib portion 22 as in the engaging element 20 of the aforementioned Embodiment 1 is not provided on an upper end surface 71a of the stem portion 71 in the Embodiment 4. In addition, in the engaging element 70 of the Embodiment 4, there is nothing protruding outward from an upper end outer peripheral edge 75 on the upper end surface 71a of the stem portion 71 except for the two micro pawl portions 73.

In the stem portion 71 of the Embodiment 4, a cross-sectional area orthogonal to an upper and lower direction gradually decreases as being away from the base portion 10 except for the upper end part of the stem portion 71, and the cross-sectional area at the upper end part of the stem portion 71 has a substantially frustum shape to be partially deformed so as to slightly increase upward.

In this case, the upper end part of the stem portion 71 is formed such that the cross-sectional area slightly increases upward as a provisional element 27 is pressed from above in the secondary molding in a manufacturing step of the molded surface fastener 4, described later. In this case, an outer peripheral side surface of the stem portion 71 is formed into a curved surface curving smoothly so as to roll back toward the upper end outer peripheral edge 75 of the stem portion 71. Therefore, loops of a female surface fastener are not caught directly on the stem portion 71 itself of the Embodiment 4.

That is, although the stem portion 71 of the Embodiment 4 has such a shape that the upper end part of the stem portion 71 slightly bulges toward the upper end outer peripheral edge 75, it is formed into a completely different configuration from the conventional mushroom type engaging element, for example, which is intentionally provided with the engaging head portion for hooking the loop. As in the case of the stem portion 21 in the above-described Embodiment 1, the stem portion 71 of the Embodiment 4 may have a frustum shape in which the cross-sectional area orthogonal to the upper and lower direction gradually decreases as being apart from the base portion 10.

Since the stem portion 71 of the Embodiment 4 as above can ensure a large cross-sectional area orthogonal to the upper and lower direction, it has a high strength. Therefore, the stem portion 71 is hardly deformed even when subjected to a large pressing force. The upper end surface 71a of the stem portion 71 is formed to be parallel to the upper surface of the base portion 10 and has an elliptical shape slightly longer in a right and left direction in a plan view of the engaging element 70. In the present invention, the upper end surface 71a of the stem portion 71 may be formed into a circular shape.

An outer peripheral edge 74 at a base end of the stem portion 71 has a circular shape with a large diameter so as to contain the upper end surface 71a of the stem portion 71 inside in a plan view of the engaging element 70. In this case, a center of the elliptical outer peripheral edge on the upper end surface 71a of the stem portion 71 and a center of the circular peripheral edge at the base end of the stem portion 71 are located on the same axis along a standing direction (upper and lower direction) of the stem portion 71.

The right and left micro pawl portions 73 provided on each engaging element 70 are integrally formed on the outer peripheral side surface of the stem portion 71. The two micro pawl portions 73 are protruded in the right and left direction toward outside from the elliptical upper end outer peripheral edge 75 of the stem portion 71 along a radial direction of the elliptical upper end surface 71a of the stem portion 71 in a plan view of the engaging element 70.

Each micro pawl portion 73 has a configuration protruding downwardly sloped toward the base portion 10 such that pawl tip ends hang downward from the outer peripheral side surface formed so as to roll back toward the upper end part of the stem portion 71. That is, the micro pawl portion 73 does not extend above a height position of an upper surface of a base end part of the micro pawl portion 73 connected to the stem portion 71 (that is, a height position of the upper end surface 71a of the stem portion 71), and protrudes in a form sloped obliquely downward toward the base portion 10. Thereby, a gap 76 is formed between the micro pawl portion 73 and the outer peripheral side surface of the stem portion 71.

The micro pawl portion 73 of the Embodiment 4 has an upper surface forming the same flat surface as the elliptical upper end surface 71a of the stem portion 71. That is, the upper surface of the engaging element 70 is flatly formed of the elliptical upper end surface 71a of the stem portion 71 and the upper surface of the micro pawl portion 73.

The micro pawl portion 73 has a rounded shape having a curved surface continuously gently curving from the flat upper surface, and has a tapered shape in which the pawl tip end portion decreases toward the pawl tip end. Particularly, in a plan view of the engaging element 70 (FIG. 22), the micro pawl portion 73 of the Embodiment 4 has a configuration in which the pawl width dimension of the micro pawl portion 73 gradually decreases from the base end part to the pawl tip end of the micro pawl portion 73.

In this case, a pawl width dimension A at the base end part of the micro pawl portion 73 is set to a size of 1/10 or more and 1/2 or less of a short diameter (minor axis) along a front and rear direction of the elliptical upper end surface 71a of the stem portion 71, preferably 1/8 or more and 1/3 or less, and further preferably 1/6 or more and 1/4 or less.

Further, in a plan view of the engaging element 70, the right and left micro pawl portions 73 are disposed within a region between the elliptical upper end outer peripheral edge 75 on the upper surface of the stem portion 71 and the circular outer peripheral edge 74 at the base end of the stem portion 71. In this case, in a plan view of the engaging element 70, only the right and left micro pawl portions 73 are formed so as to bulge on an outside of the upper end outer peripheral edge 75 on the upper surface of the stem portion 71.

Further, in a plan view of the engaging element 70, a protrusion length B of the micro pawl portion 73 from the upper end outer peripheral edge 75 of the stem portion 71 to the pawl tip end is set to be a size of 1/2 or less of the short diameter at the elliptical upper end surface 71a of the stem portion 71, preferably 1/3 or less, and further preferably 1/4 or less.

In the Embodiment 4, a range of a specific size of each portion and a specific range of forming density of the engaging element 70 are substantially the same as in the Embodiment 1.

That is, a height dimension C of the engaging element 70 in an upper and lower direction from the upper surface of the base portion 10 is set to be 0.04 mm or more and 1.5 mm or less, preferably 0.2 mm or more and 1.0 mm or less. In the case of the Embodiment 4, the height dimension C of the engaging element is the same as a height dimension of the stem portion.

A short diameter F1 along a front and rear direction of the elliptical upper end surface 71a of the stem portion 71 is set to be 0.1 mm or more and 0.5 mm or less. A long diameter F2 along the right and left direction of the elliptical upper end surface 71a of the stem portion 71 is set to be larger than the short diameter F1 to be 0.1 mm or more and 0.5 mm or less. In the Embodiment 4, the upper end surface 71a of the stem portion 71 may be formed in a circular shape having a diameter of 0.1 mm or more and 0.5 mm or less. A diameter G of the circular outer peripheral edge at the base end of the stem portion 71 is set to be 0.15 mm or more and 0.55 mm or less.

Regarding the micro pawl portion 73 of the Embodiment 4, the pawl width dimension A of the micro pawl portion 73 is set to be 0.01 mm or more and 0.1 mm or less, and preferably 0.03 mm or more and 0.08 mm or less. In a plan view of the engaging element 70, the protrusion length B of the micro pawl portion 73 is set to be 0.01 mm or more and 0.1 mm or less. A pawl height dimension H of the micro pawl portion 73 in an upper and lower direction from the upper end surface 71a of the stem portion 71 to the pawl tip end of the micro pawl portion 73 is set to be 0.01 mm or more and 0.1 mm or less.

A size J of the gap 76 formed between the micro pawl portion 73 and the outer peripheral side surface of the stem portion 71 at the height position of the pawl tip end of the micro pawl portion 73 is set to be 0.01 mm or more and 0.1 mm or less. The protruding inclination angle θ of the micro pawl portion 73 formed by the pawl back surface of the micro pawl portion 73 and the outer peripheral side surface of the stem portion 71 is larger than 0°, preferably 20° to 80°, and further preferably 30° to 60°.

An area of the elliptical upper end surface 71a of the stem portion 71 is set to be 0.01 $mm^2$ or more and 0.25 $mm^2$ or less. An area of the micro pawl portion 73 which can be confirmed in a plan view of the engaging element 70 is set to be 0.005 $mm^2$ or more and 0.05 $mm^2$ or less, and is set at 90% or less of the area of the elliptical upper end surface 71a of the stem portion 71, preferably 50% or less, and further preferably 20% or less.

Further, in the Embodiment 4, an interval between the engaging elements 70 adjacent to each other in the front and rear direction (MD) and an interval between the engaging elements 70 adjacent to each other in the right and left direction (CD) can be set at 0.3 mm to 0.8 mm, preferably 0.35 mm to 0.6 mm, and further preferably 0.35 mm to 0.5 mm. Therefore, the forming density of the engaging elements 70 on the upper surface of the base portion 10 is can be set to be 150 pieces/$cm^2$ or more and 1000 pieces/$cm^2$ or less, preferably 150 pieces/$cm^2$ or more and to 300 pieces/$cm^2$ or less, and further preferably 200 pieces/$cm^2$ or more and 280 pieces/$cm^2$ or less.

Figure 26:
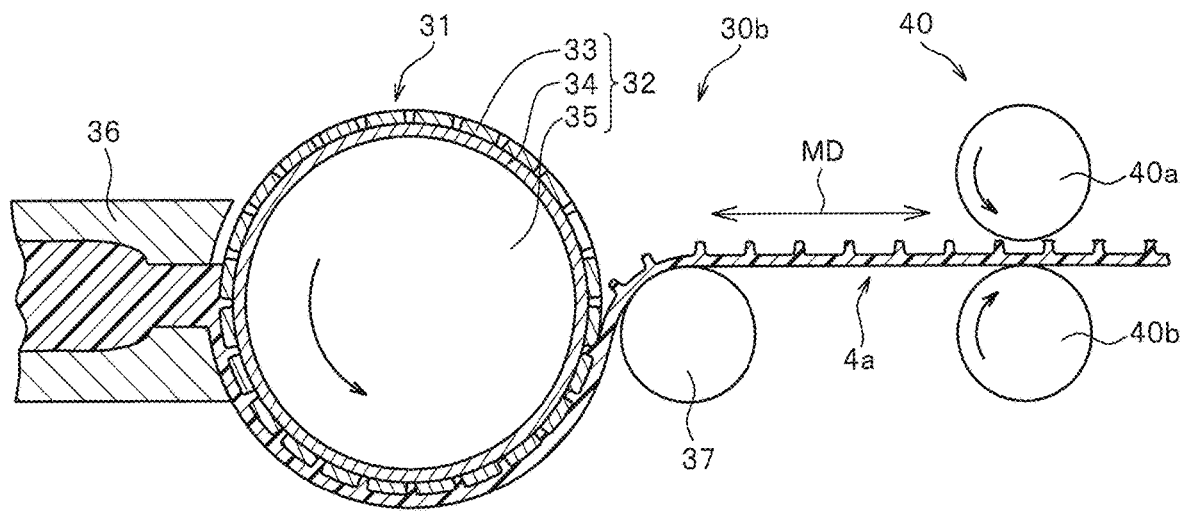
FIG. 26 is a schematic view schematically illustrating a manufacturing apparatus of the molded surface fastener in Embodiment 4.
Figure 27:
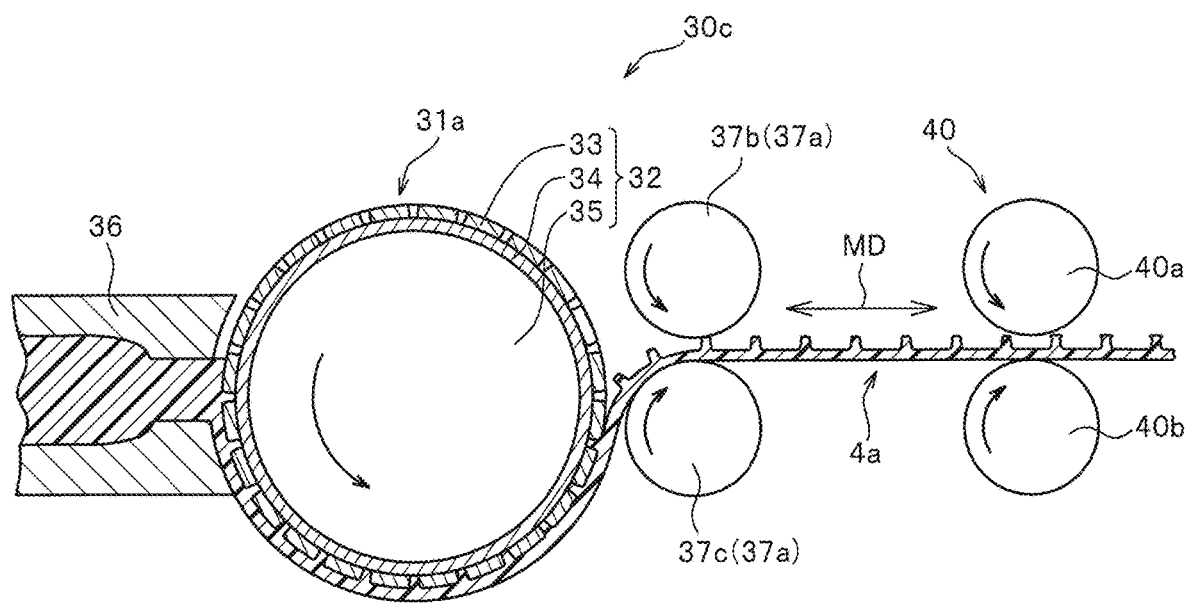
FIG. 27 is a schematic view schematically illustrating another manufacturing apparatus of the molded surface fastener in the Embodiment 4.

The molded surface fastener 4 of the Embodiment 4 as described above is manufactured using a manufacturing apparatus 30b shown in FIG. 26 or a manufacturing apparatus 30c according to a modification example shown in FIG. 27.

First, the manufacturing apparatus 30b shown in FIG. 26 includes a molding apparatus 31 conducting a primary molding step and a heat press apparatus 40 heating and pressing the primary molded body 1a molded in the primary molding step. In this case, the molding apparatus 31 as that of the above-described Embodiment 1 is used as a molding apparatus 31 of the Embodiment 4.

The heat press apparatus 40 of the Embodiment 4 includes a pair of upper and lower press rollers (calendar rollers) 40a, 40b. The upper side press roller 40a and the lower side press roller 40b are disposed to face each other with a predetermined interval. In this case, the interval between the upper side press roller 40a and the lower side press roller 40b can be adjusted by a height adjusting means (not shown). In the case of the Embodiment 4, it is adjusted in accordance with the height dimension from a lower surface (back surface) of the base portion 10 to the elliptical upper end surface 71a of the stem portion 71 of the molded surface fastener 4 to be manufactured.

The upper side press roller 40*a* includes a heating source (not shown) inside. In this case, a surface temperature of the upper side press roller 40*a* is set to a temperature at which a synthetic resin forming the molded surface fastener 4 can be softened. Specifically, it is set to be a predetermined temperature equal to or higher than a melting point of the synthetic resin−40° C. and lower than the temperature of the melting point−10° C. Further, the upper side press roller 40*a* is disposed so as to rotate counterclockwise in FIG. 26. The outer peripheral surface of the upper side press roller 40*a* serves as a surface pressing the heated provisional element 27 of the primary molded body 1*a* molded in the primary molding step from above.

The lower side press roller 40*b* is disposed so as to rotate in a clockwise direction in FIG. 26, and serves as a supporting surface for supporting the primary molded body 1*a* to be conveyed from below. In the present invention, it is also possible to use an upper side belt mechanism and/or a lower side belt mechanism (not shown) instead of the upper side press roller 40*a* and/or the lower side press roller 40*b*. In this case, the upper side belt mechanism and the lower side belt mechanism have an endless belt and a pair of right and left rotating rollers around which the endless belt is wound and rotate the endless belt in one direction.

In the case of manufacturing the molded surface fastener 4 of the Embodiment 4 using the manufacturing apparatus 30*b* including the molding apparatus 31 and the heat press apparatus 40 as described above, firstly, the primary molding step for molding the primary molded body 1*a* is conducted by the molding apparatus 31. The primary molding step of the Embodiment 4 is conducted in the same manner as the primary molding step of the Embodiment 1 described above. Thereby, the primary molded body 1*a* in which the plurality of the provisional elements 27 shown in FIG. 11 stand on the base portion 10 is molded.

The primary molded body 1*a* molded by the molding apparatus 31 is peeled off from the outer peripheral surface of a die wheel 32 by a pickup roller 37 and then conveyed toward the heat press apparatus 40 conducting the secondary molding step, and introduced between the upper side press roller 40*a* and the lower side press roller 40*b* of the heat press apparatus 40.

In this case, as shown in FIG. 11, the primary molded body 1*a* after being peeled off from the die wheel 32 includes the provisional element 27 in which the right and left protruded portions 28 protrude substantially in parallel with the upper surface of the base portion 10 from both end edges of the rib portion 22. Therefore, the primary molded body 1*a* conveyed to the secondary molding step is introduced between the upper side press roller 40*a* and the lower side press roller 40*b* in a state that the right and left protruded portions 28 protrude substantially in parallel with the upper surface of the base portion 10.

When the primary molded body 1*a* passes between the upper side press roller 40*a* and the lower side press roller 40*b*, the upper end part of the stem portion 21, the rib portion 22, and a part of the right and left protruded portions 28 of the provisional element 27 are heated and softened by the upper side press roller 40*a*, and pressed from above.

Thereby, the upper end part of the stem portion 21, the rib portion 22, and a part of the right and left protruded portions 28 of the provisional element 27 are squashed and thermally deformed so as to be flattened while spreading as a whole. Thereby, the elliptical upper end surface 71*a* of the stem portion 71 and the upper surface of the micro pawl portion 73 (that is, the upper surface of the engaging element 70) are formed on the same plane.

At this time, the upper end surface 71*a* of the stem portion 71 to be flattened is flattened so as to expand radially larger than the circular upper end surface 21*a* of the stem portion 21 of the provisional element 27. Particularly in the case of the Embodiment 4, the upper end surface 71*a* of the stem portion 71 to be flattened expands such that the right and left direction (CD) where the rib portion 62 is formed is slightly longer than the front and rear direction (MD), thereby, it is deformed from a circular shape in the state of the provisional element 27 to an elliptical shape slightly longer in the right and left direction.

Figure 21:
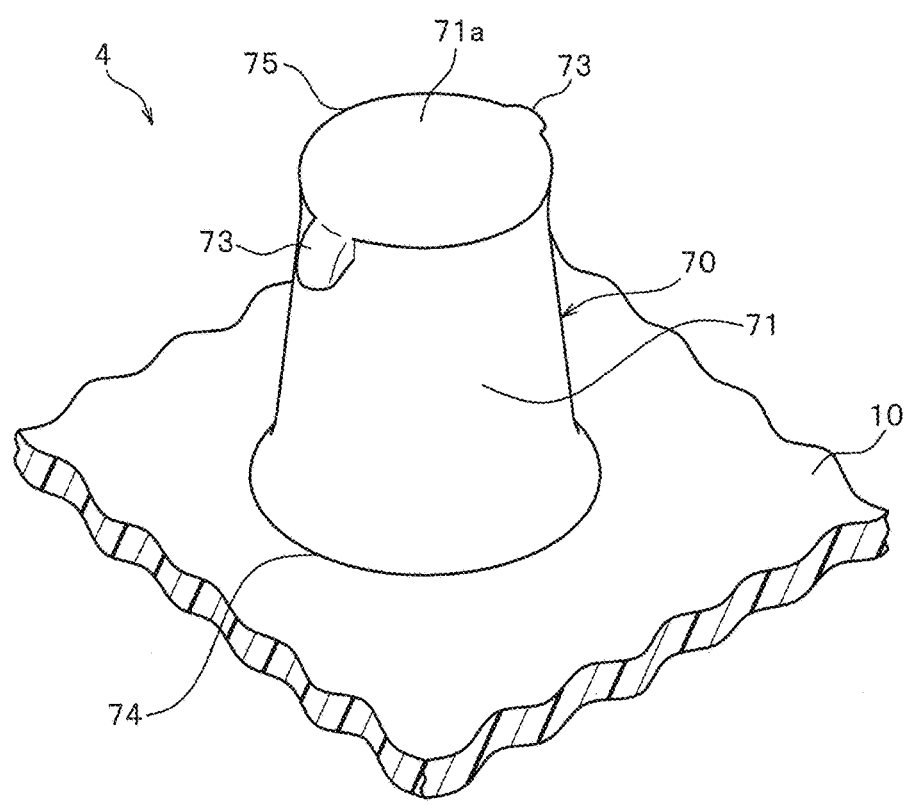
FIG. 21 is a perspective view illustrating an engaging element of the molded surface fastener.
Figure 22:
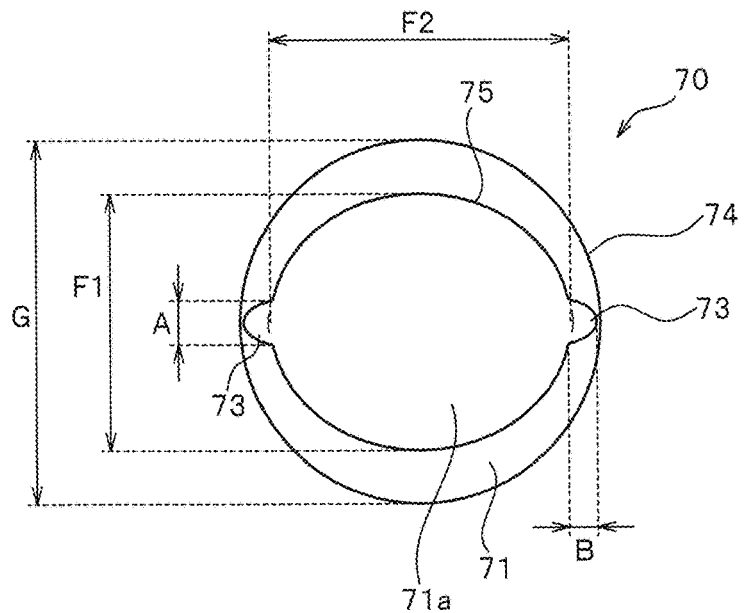
FIG. 22 is a plan view illustrating the engaging element only.
Figure 23:
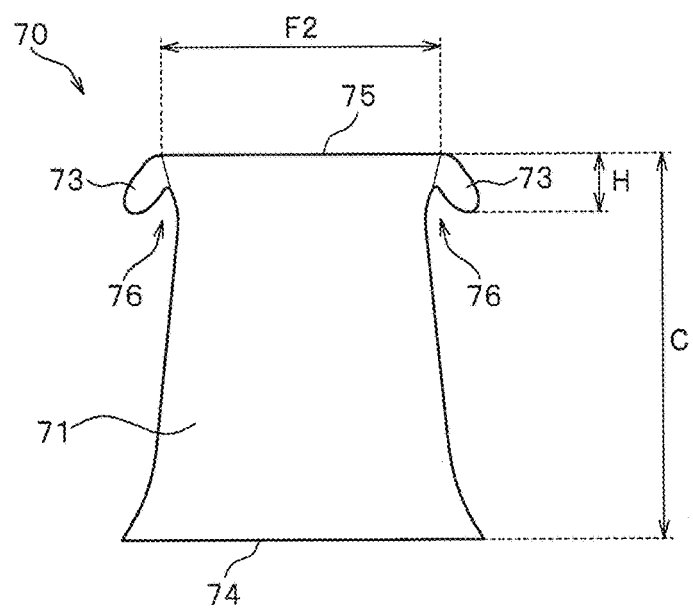
FIG. 23 is a front view of the engaging element only when viewed from a front and rear direction (machine direction: MD) of the molded surface fastener.
Figure 24:
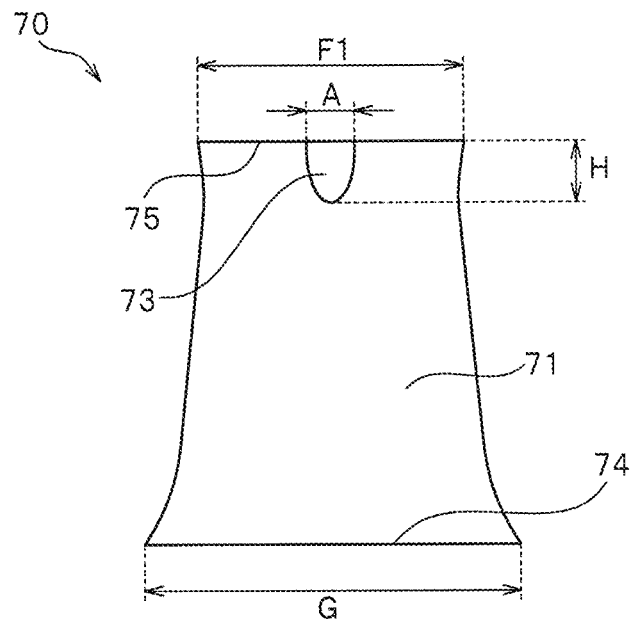
FIG. 24 is a side view of the engaging element only when viewed from a right and left direction (crossing direction: CD) of the molded surface fastener.

At the same time that the upper end surface 71*a* of the stem portion 71 is flattened, the right and left protruded portions 28 are pressed by the outer peripheral surface of the upper side press roller 40*a* while being heated and hanging, thereby the right and left micro pawl portions 73 protruding toward the base portion 10 from the outer peripheral side surface of the stem portion 71 are formed. As a result, the molded surface fastener 4 of the Embodiment 4 shown in FIG. 21 is manufactured.

In the Embodiment 4, as described above, the secondary molding step by the upper side press roller 40*a* and the lower side press roller 40*b* is conducted with respect to the primary molded body 1*a* molded in the primary molding step (that is, the primary molded body 1*a* in which the protruded portion 28 protrudes substantially in parallel with the upper surface of the base portion 10), thereby the molded surface fastener 4 is manufactured. However, in the present invention, after the primary molded body 1*a* molded in the primary molding step is conveyed horizontally, and the right and left protruded portions 28 of the provisional element 27 are partially bent and deformed by its own weight and/or blowing a hot air from above so as to hang downward as described in the Embodiment 1, the secondary molding step by the upper side press roller 40*a* and the lower side press roller 40*b* may be conducted.

In this case, the primary molded body is introduced between the upper side press roller 40*a* and the lower side press roller 40*b* in the secondary molding step in a state that the right and left protruded portions 28 of the provisional element 27 are partially deformed so as to hang toward the base portion 10. It also makes it possible to manufacture the molded surface fastener 4 of the Embodiment 4 shown in FIG. 21 (or the molded surface fastener in which the right and left micro pawl portions further hang toward the base portion than the case of the Embodiment 4).

On the other hand, the manufacturing apparatus 30*c* according to the modification example shown in FIG. 27 includes a molding apparatus 31*a* conducting a primary molding step and a heat press apparatus 40 heating and pressing a primary molded body 1*a* molded in the primary molding step. In this case, the same molding apparatus 31*a* according to the modification example of the above-described Embodiment 1 is used as the molding apparatus 31*a*. Further, the heat press apparatus 40 is the same as the heat press apparatus 40 of the manufacturing apparatus 30*b* shown in FIG. 26.

In the case of manufacturing the molded surface fastener 4 of the Embodiment 4 using the manufacturing apparatus 30*c*, the primary molding step is conducted by extruding a molten synthetic resin material from an extrusion nozzle 36 toward an outer peripheral surface of a die wheel 32 to mold the primary molded body 1*a*. Subsequently, the molded primary molded body 1*a* is continuously peeled off from the outer peripheral surface of the die wheel 32 by pickup rollers 37*a*, and then passes between an upper side holding roller 37*b* and a lower side holding roller 37*c* of the pickup rollers 37a. Thus, right and left protruded portions 28 of a provisional element 27 are protruded downward from side end edges of a rib portion 22, or protruded in a horizontal direction substantially in parallel with an upper surface of a base portion 10.

Subsequently, the primary molded body 1a is conveyed toward the heat press apparatus 40 conducting a secondary molding step, and is introduced between the upper side press roller 40a and the lower side press roller 40b of the heat press apparatus 40. Thus, the upper end surface 71a of the stem portion 71 is flattened, and the right and left protruded portions 28 are pressed by the outer peripheral surface of the upper side press roller 40a while being heated and hanging, thereby the molded surface fastener 4 is manufactured. Therefore, in the Embodiment 4, the molded surface fastener 1 of the Embodiment 4 shown in FIG. 21 can be stably manufactured by using the manufacturing apparatus 30c shown in FIG. 27.

In the molded surface fastener 4 of the Embodiment 4 manufactured as described above, each engaging element 70 has a characteristic configuration formed of only by a stem portion 71 and two micro pawl portions 73 protruding from an outer peripheral side surface of the stem portion 71 toward the base portion 10 so as to hang downward. The configuration of the engaging element 70 of the Embodiment 4 is completely different from the configuration of each of the conventional J-shaped, palm tree-shaped, and mushroom-shaped engaging elements.

According to the molded surface fastener 4 of the Embodiment 4 having the engaging element 70 with such a characteristic configuration, since strength of the stem portion 71 is increased, the shape of the engaging element 70 can be stably held even when it receives a large pressing force. Further, the right and left micro pawl portions 73 protrude toward the base portion 10 outward from the outer peripheral side surface of the stem portion 71. Therefore, in the molded surface fastener 4 of the Embodiment 4, it is possible to smoothly insert the engaging element 70 toward loops of a female surface fastener, and to easily hook the loop to the engaging element 70 for stable engagement. Further, the engaged loop can hardly come off from the engaging element 70.

Accordingly, the molded surface fastener 4 of the Embodiment 4 can have a high peel strength and a high shear strength with respect to the female surface fastener. Further, in the molded surface fastener 4 of the Embodiment 4, the flat elliptical upper end surface 71a of the stem portion 71 in the engaging element 70 is exposed with a larger area than that of the molded surface fastener 1 of the above mentioned Embodiment 1, for example. For this reason, it is possible to stably obtain a pleasant texture and a touch comfort.

In the Embodiment 4, the molded surface fastener 4 in which the two micro pawl portions 73 in right and left are provided on the outer peripheral side surface of the stem portion 71 in the engaging element 70 is described. On the other hand, in the present invention, as described in the above Embodiments 1 to 3, for example, as a configuration of the engaging element in which the micro pawl portions protrude from the rib portions, it is possible to adopt the configuration of the engaging element 50 of the Embodiment 2 including the four micro pawl portions 53 protruding toward front, rear, right, and left and the configuration of the engaging element 60 of the Embodiment 3 including the eight micro pawl portions 63 regularly protruding in eight directions, in addition to the configuration of the engaging element 20 of the Embodiment 1 including the two micro pawl portions 23 protruding toward right and left.

Figure 28:
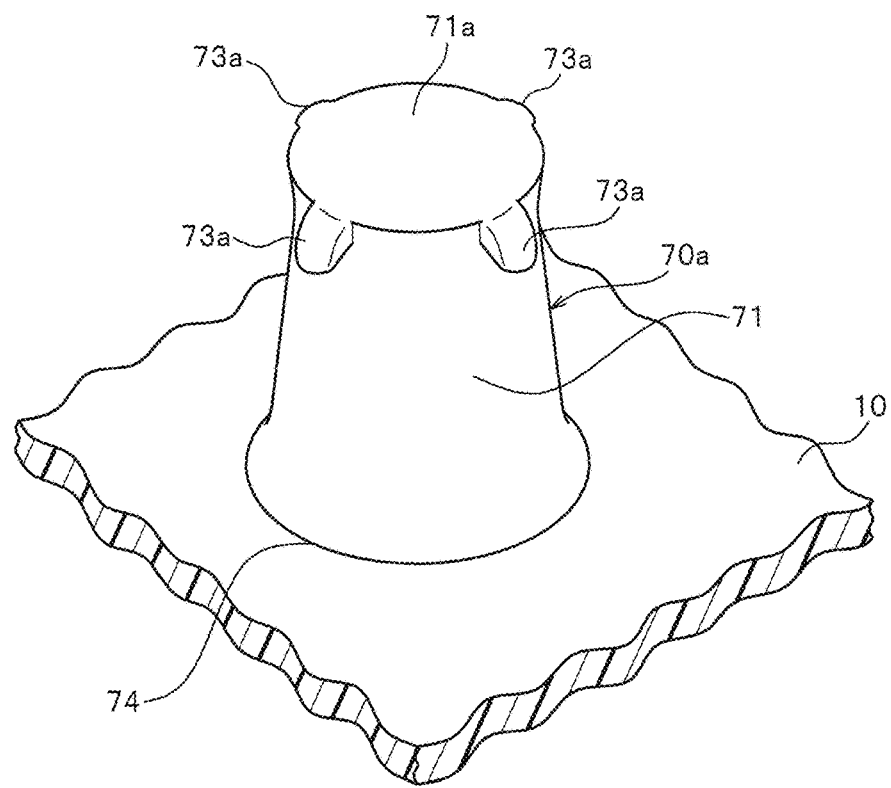
FIG. 28 is a perspective view illustrating an engaging element of a molded surface fastener according to Embodiment 5 of the present invention.
Figure 29:
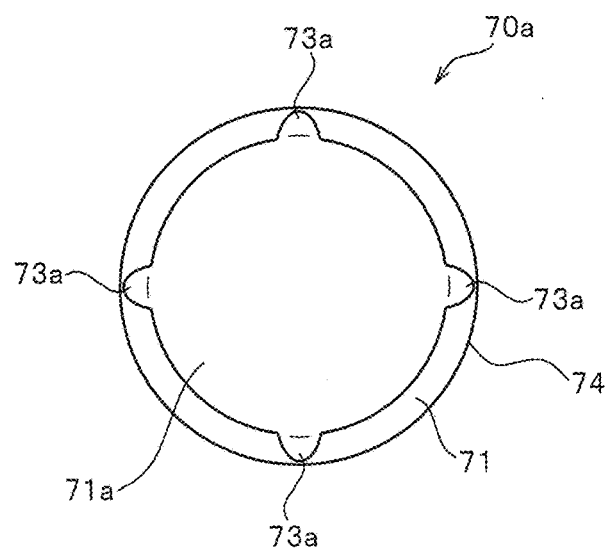
FIG. 29 is a plan view illustrating the engaging element only.

That is, it is possible to adopt the configuration of the engaging element 70a including the four micro pawl portions 73a protruding toward front, rear, right, and left as shown in FIGS. 28 and 29, for example, or the configuration of the engaging element including the flat upper surface of the stem portion and the eight micro pawl portions regularly protruding in eight directions (not shown).

Further, in the present invention, configurations such as the number, a shape, a size, an arrangement, and the like of the micro pawl portions provided on the engaging element are not limited to those of the Embodiments 1 to 4 described above, and can be changed arbitrarily according to the purpose of use of the molded surface fastener.

In the present invention, for example, regarding the die wheel 32 of the molding apparatus 31 or the molding apparatus 31a conducting the aforementioned primary molding step, it is possible to arbitrarily change the forming pitch of the concave groove portions 41, 42, 43 provided on the inner side cylindrical body 34, 34a, 34b with respect to the forming pitch of the penetration holes 38 in the circumferential direction (MD) and the axial direction (CD) provided on the outer side cylindrical body 33 so as to make it small intentionally (refer to a modification example 1 described later, for example). As a result, it is possible to increase the number of the micro pawl portions 23, 53, 63, 73, 73a provided on each of the engaging elements 20, 50, 60, 70, 70a and to make the number of the micro pawl portions 23, 53, 63, 73, 73a different between each of the engaging elements 20, 50, 60, 70, 70a.

In the Embodiments 1 to 4 described above, the plurality of concave groove portions 41, 42, 43 having the same groove width and the same groove depth mutually are formed on the one inner side cylindrical body 34, 34a, 34b. However, in the present invention, it is also possible to provide a plurality of concave groove portions 41, 42, 43 having different groove widths or different groove depths mutually in one inner side cylindrical body 34, 34a, 34b. Thereby, it is possible to make protrusion angles and sizes of the micro pawl portions 23, 53, 63, 73, 73a different mutually among each of the engaging elements 20, 50, 60, 70, 70a. Furthermore, it is also possible to provide a plurality of micro pawl portions 23, 53, 63, 73, 73a protruding at different angles mutually and a plurality of micro pawl portions 23, 53, 63, 73, 73a having different sizes mutually with respect to the one engaging element 20, 50, 60, 70, 70.

Further, in the present invention, a shape and size of the micro pawl portions can be easily changed by changing forming pattern of the concave groove portions provided on the inner side cylindrical body of the molding apparatus conducting the primary molding step. Here, a representative modification example of the forming pattern of the concave groove portions provided on the inner side cylindrical body will be described with reference to the drawings.

FIGS. 30 to 33 are schematic views of the main part illustrating a positional relationship between a concave groove portion provided in an inner side cylindrical body and a penetration hole provided on an outer side cylindrical body in each modification example. In these figures, two circles represent outer peripheral edges of the penetration hole disposed on the inner peripheral surface of the outer side cylindrical body. In addition, the white part represents the concave groove portions provided on the outer peripheral surface of the inner side cylindrical body, and the gray part represents the part of the cylindrical outer peripheral surface of the inner side cylindrical body where the concave groove portion is not provided.

Figure 30:
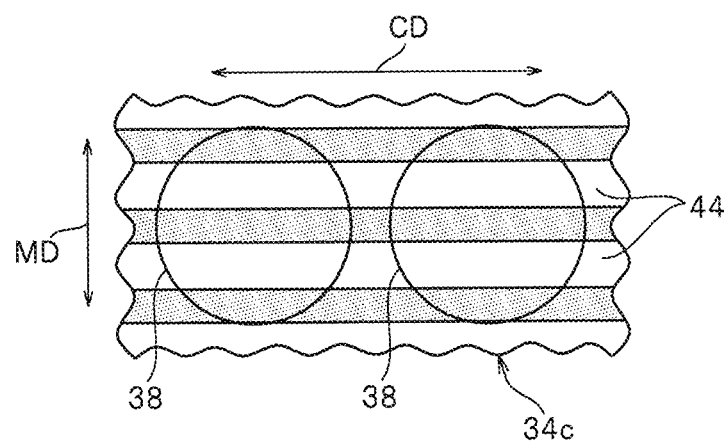
FIG. 30 is a schematic view of a main part illustrating a positional relationship between a penetration hole of an outer side cylindrical body and a concave groove portion of an inner side cylindrical body according to a modification example 1.

The inner side cylindrical body 34c according to a modification example 1 shown in FIG. 30 is formed to have a larger groove width of the concave groove portion 44 than that of the case of Embodiment 1, and to have a smaller forming pitch of the concave groove portions 44 than that of the case of Embodiment 1. More specifically, a plurality of concave groove portions 44 linearly disposed along an axial direction (CD) are concaved on the outer peripheral surface of the inner side cylindrical body 34c according to the modification example 1 so as to form a striped pattern. In the above-described Embodiment 1, for example, as shown in FIG. 8, the only one concave groove portion 41 concaved along a C direction on the inner side cylindrical body 34 is formed at a position along a diameter of the penetration hole 38 with respect to one cylindrical penetration hole 38 of the outer side cylindrical body 33.

On the other hand, in this modification example 1, an interval (forming pitch) between each of the concave groove portions 44 is made smaller than that of the above-described Embodiment 1, therefore, the plurality of concave groove portions 44 (two concave groove portions 44 in this case), which are thicker than the aforementioned Embodiment 1, is formed so as to cross with respect to the one circular penetration hole 38 of the outer side cylindrical body 33.

The molded surface fastener is manufactured using the inner side cylindrical body 34c in which the plurality of concave groove portions 44 in the C direction with respect to the one circular penetration hole 38 of the outer side cylindrical body 33 as in the modification example 1, thereby, the molded surface fastener in which three or more micro pawl portions are protrudingly provided on the engaging element can be easily obtained. Further, in this case, since the concave groove portions 44 of the inner side cylindrical body 34c are provided along the C direction, the plurality of micro pawl portions 73 provided on the engaging element 70 are formed so as to protrude symmetrically in the right and left direction with reference to a diameter (or minor axis) along a front and rear direction of the upper end surface of the stem portion.

Figure 31:
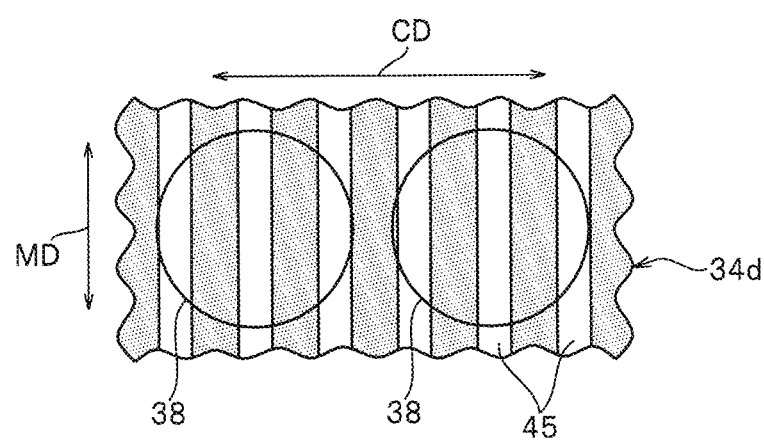
FIG. 31 is a schematic view of a main part illustrating a positional relationship between a penetration hole of an outer side cylindrical body and a concave groove portion of an inner side cylindrical body according to a modification example 2.
Figure 32:
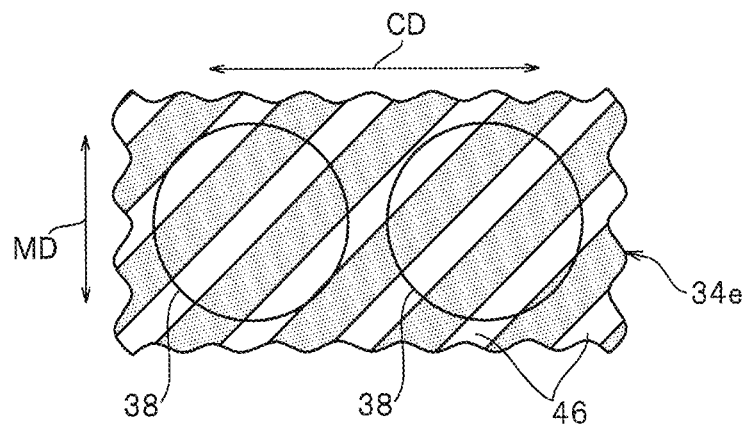
FIG. 32 is a schematic view of a main part illustrating a positional relationship between a penetration hole of an outer side cylindrical body and a concave groove portion of an inner side cylindrical body according to a modification example 3.

Furthermore, in the present invention, it is also possible to manufacture the molded surface fastener in which a plurality of micro pawl portions are provided so as to protrude symmetrically on the engaging element by providing the inner side cylindrical body 34d with only a plurality of the concave groove portions 45 along a circumferential direction of a cylinder to be an M direction as shown by modification example 2 in FIG. 31, for example, and by providing the inner side cylindrical body 34e with only a plurality of the concave groove portions 46 inclined at a predetermined angle with respect to the C direction or the M direction as shown by modification example 3 in FIG. 32, for example, instead of forming the concave groove portions in the C direction on the outer peripheral surface of the inner side cylindrical body.

Even in the case of these modification examples 1 to 3 (FIGS. 30 to 32), it is also possible to change the number of the concave groove portions 44,45,46 crossing one circular penetration hole 38 of the outer side cylindrical body 33 by changing the size of the each of the penetration hole 38 formed on the outer side cylindrical body 33 and changing the groove width and forming pitch of the concave groove portions 44, 45, 46 formed on the inner side cylindrical bodies 34c, 34d, 34e, and the like. Further, it is also possible to provide a plurality of concave groove portions 44, 45, 46 having different groove widths on the inner side cylindrical bodies 34c, 34d, 34e, or to provide the plurality of concave groove portions 44, 45, 46 with different forming pitches.

Figure 33:
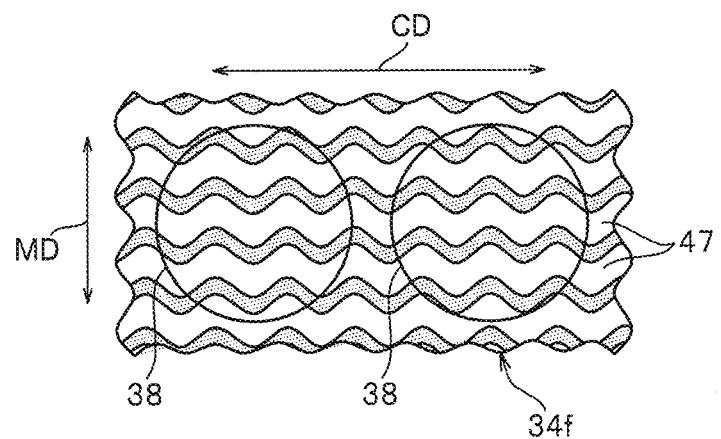
FIG. 33 is a schematic view of a main part illustrating a positional relationship between a penetration hole of an outer side cylindrical body and a concave groove portion of an inner side cylindrical body according to a modification example 4.
Figure 34:
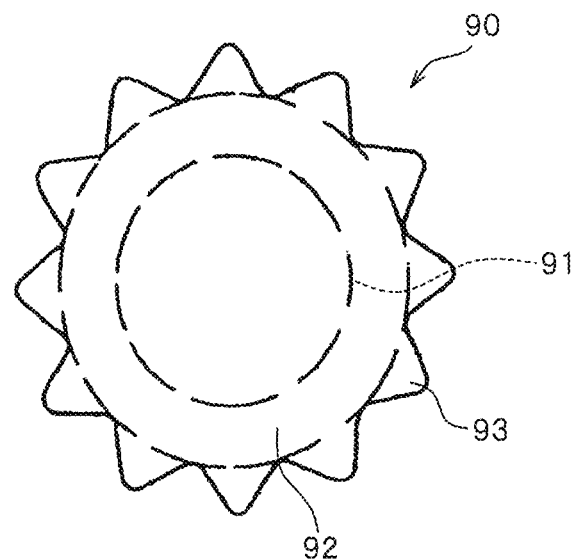
FIG. 34 is a plan view illustrating an engaging element formed on a conventional molded surface fastener.
Figure 35:
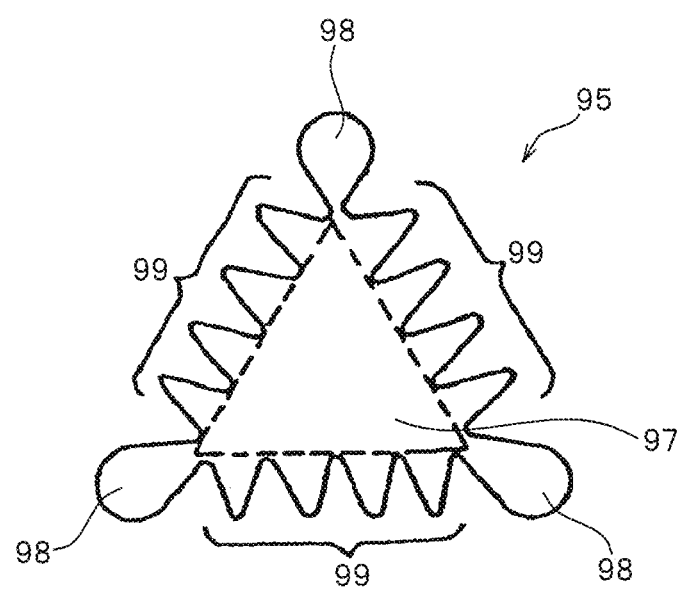
FIG. 35 is a plan view illustrating an engaging element formed on another conventional molded surface fastener.

Next, in a modification example 4 shown in FIG. 33, a plurality of concave groove portions 47 meandering in a wave shape along the C direction are concaved at a predetermined forming pitch on the outer peripheral surface of the inner side cylindrical body 34f. In the modification example 4, it is possible to form one or a plurality of concave groove portions 47 with respect to one circular penetration hole 38 of an outer side cylindrical body 33 by changing the size of a penetration hole 38 formed on the outer side cylindrical body 33, groove width and forming pitch of the concave groove portions 47, and the like.

Furthermore, in this modification example 4, the plurality of concave groove portions 47 meandering in the wave-shaped are concaved along the C direction on the outer peripheral surface of the inner side cylindrical body 34f. In the present invention, however, the plurality of concave groove portions 47 meandering in the wave shape can be concaved along a circumferential direction of the cylinder which is M direction, or an inclined direction at a predetermined angle with respect to the C direction or the M direction.

It is possible to stably manufacture a molded surface fastener in which a plurality of micro pawl portions are provided on an engaging element also by conducting a primary molding process using the inner side cylindrical body 34f in which the plurality of concave groove portions 47 meandering in the wave shape are concaved as in this modification example 4.

In each of the molded surface fasteners manufactured using the inner side cylindrical bodies 34c, 34d, 34e, and 34f shown in the modification examples 1 to 4 described above, the stem portion of the engaging element is formed thick, and the flat upper end surface of the stem portion is widely exposed upward. Furthermore, each of the engaging elements is provided with at least two micro pawl portions protruding toward the base portion. Therefore, it is possible to stably have a high peel strength and a high shear strength with respect to the female surface fastener having loops, and to make the texture of the upper surface of the molded surface fastener better.

In the Embodiments 1-4 and the modification examples 1-4 described above, a case in which the primary molding step of the molded surface fastener is conducted using the molding apparatus 31 including the die wheel 32 shown in FIGS. 7 and 26 or the molding apparatus 31 including the die wheel 32 and the pickup rollers 37a shown in FIGS. 12 and 27 is described. However, in the present invention, it is also possible to use a molding apparatus with other configurations in the primary molding step of the molded surface fastener.

As a molding apparatus for molding a primary molded body, for example, it is possible to use an apparatus including a die wheel drivingly rotating in one direction, a press wheel which is disposed with a predetermined interval from the die wheel and is drivingly rotated in a direction opposite to that of the die wheel, and an extrusion nozzle for discharging a molten synthetic resin material toward between the die wheel and the press wheel. Further, the molding apparatus can further include the pickup rollers 37a shown in FIGS. 12 and 27.

In this case, the die wheel of the molding apparatus has the same structure as the die wheel 32 described in the Embodiment 1 and the like. That is, as described in the Embodiment 1 and the like, the die wheel according to this modification example includes an outer side cylindrical body in which a plurality of circular penetration holes are drilled, an inner side cylindrical body in which a plurality of concave groove portions are concaved on an outer peripheral surface in a predetermined pattern, and a rotation driving roller for rotating the outer side cylindrical body and the inner side cylindrical body in one direction.

Further, in the present invention, as a molding apparatus according to another modification example, for example, an apparatus including a molding side belt mechanism rotating in one direction, press side belt mechanism disposed with a predetermined interval from the molding side belt mechanism and rotating and travelling in a direction opposite to that of the molding side belt mechanism, and an extrusion nozzle disposed facing to a belt outer peripheral surface of the molding side belt mechanism and continuously discharging a molten synthetic resin material may be used. Further, the molding apparatus can further include the pickup rollers 37*a* shown in FIGS. 12 and 27.

In this case, the molding side belt mechanism includes an outer side endless belt to be a mold member, an inner side endless belt disposed in close contact with an inside of the outer side endless belt, and a pair of rotating rollers around which the outer side endless belt and the inner side endless belt are wound, and which rotates and travels the outer side endless belt and the inner side endless belt. In this molding side belt mechanism, it is possible to synchronously rotate the outer side endless belt and the inner side endless belt.

Further, on the outer side endless belt, a plurality of penetration holes similar to the penetration holes 38 provided on the outer side cylindrical body 33 (see FIGS. 8 to 10) of the Embodiment 1 are drilled in order to mold the stem portions of the primary molded body. On the outer peripheral surface of the inner side endless belt, a plurality of concave groove portions are concaved in a predetermined pattern in order to mold rib portions and protruded portions of the primary molded body. Further, the press side belt mechanism includes an endless belt for pressing and a pair of rotating rollers around which the endless belt for pressing is wound, and which rotates and travels the endless belt for pressing.

It is also possible to stably manufacture the molded surface fastener according to the present invention described in the above-mentioned Embodiments 1 to 4, also by conducting the primary molding step for molding the primary molded body using the molding apparatus including the die wheel and the press wheel as described above and the molding apparatus including the molding side belt mechanism and the press side belt mechanism.

1 Molded surface fastener
1*a* Primary molded body
2,3,4 Molded surface fastener
4*a* Primary molded body
10 Base portion
15 Loop
20 Engaging element (Male engaging element)
21 Stem portion
21*a* Upper end surface
22 Rib portion
23 Micro pawl portion
24 Outer peripheral edge at base end of stem portion
25 Upper end outer peripheral edge at upper surface of stem portion
26 Gap
27 Provisional element
28 Protruded portion (Provisional micro pawl portion)
30,30*a* Manufacturing apparatus
30*b*,30*c* Manufacturing apparatus
31,31*a* Molding apparatus
32 Die wheel
33 Outer side cylindrical body (Outer side sleeve)
34 Inner side cylindrical body (Inner side sleeve)
34*a*-34*f* Inner side cylindrical body (Inner side sleeve)
35 Rotation driving roller
36 Extrusion nozzle
37 Pickup roller
37*a* Pickup roller
37*b* Upper side holding roller
37*c* Lower side holding roller
38 Penetration hole (Circular penetration hole)
39*a* Groove overlapped part
39*b* Close contact part
40 Heat press apparatus
40*a* Upper side press roller
40*b* Lower side press roller
41 Concave groove portion
42 Concave groove portion
42*a* First concave groove portion
42*b* Second concave groove portion
43 Concave groove portion
43*a* First concave groove portion
43*b* Second concave groove portion
43*c* Third concave groove portion
43*d* Fourth concave groove portion
44,45 Concave groove portion
46,47 Concave groove portion
50 Engaging element (Male engaging element)
52 Rib portion
52*a* First rib portion
52*b* Second rib portion
53 Micro pawl portion
60 Engaging element
62 Rib portion
62*a* First rib portion
62*b* Second rib portion
62*c* Third rib portion
62*d* Fourth rib portion
63 Micro pawl portion
70,70*a* Engaging element
71 Stem portion
71*a* Upper end surface
73,73*a* Micro pawl portion
74 Outer peripheral edge at base end of stem portion
75 Upper end outer peripheral edge at upper surface of stem portion
76 Gap
A Pawl width dimension of micro pawl portion at base end part
B Protrusion length of micro pawl portion of engaging element in a plan view
C Height dimension of engaging element
D Height dimension of stem portion
E Height dimension of rib portion
F Diameter of stem portion at circular upper end surface
F1 Short diameter of stem portion at elliptical upper end surface
F2 Long diameter of stem portion at elliptical upper end surface
G Diameter of circular outer peripheral edge of stem portion at base end
H Pawl height dimension of micro pawl portion
J Size of gap between micro pawl portion and stem portion
θ Protruding inclination angle of micro pawl portion.

The invention claimed is:

1. A manufacturing method of a molded surface fastener made of synthetic resin in which a plurality of engaging elements stand on an upper surface of a flat plate-shaped base portion, the manufacturing method including a primary molding step for molding a primary molded body comprising the base portion and a plurality of provisional elements standing on the base portion and a secondary molding step for molding the molded surface fastener by heating at least a part of the provisional elements of the primary molded body and compressing them from above, wherein the manufacturing method including:
   in the primary molding step, molding the primary molded body in which each of the provisional elements comprises a columnar stem portion standing on the base portion, a rib portion protruding on an upper surface of the stem portion, and at least two protruded portions protruding from the rib portion toward an outside of an upper end outer peripheral edge of the stem portion along a direction crossing with respect to a standing direction of the stem portion, and in which the upper surface of the stem portion excluding the part provided with the rib portion is exposed upward; and
   in the secondary molding step, forming the engaging element which comprises a stem portion and micro pawl portions protruding from an outer peripheral side surface of the stem portion toward the base portion and is capable of engaging loops of a female surface fastener only with the micro pawl portions by compressing at least a part of the protruded portions and the rib portion of the primary molded body from above.

2. The manufacturing method of the molded surface fastener according to claim 1, including:
   molding the primary molded body in the primary molding step using a die wheel provided with an outer side cylindrical body in which a plurality of penetration holes penetrating from an outer peripheral surface to an inner peripheral surface are drilled, and an inner side cylindrical body disposed in close contact with an inner peripheral surface of the outer side cylindrical body concentrically;
   in which a plurality of concave groove portions are concaved on an outer peripheral surface of the inner side cylindrical body; and
   an outer peripheral edge of a penetration hole in an inner peripheral surface of the outer side cylindrical body includes a part overlapping and crossing the concave groove portion of the inner side cylindrical body and a part contacting closely with an outer peripheral surface of the inner side cylindrical body.

* * * * *

UNITED STATES PATENT AND TRADEMARK OFFICE
CERTIFICATE OF CORRECTION

PATENT NO. : 11,363,857 B2
APPLICATION NO. : 16/807341
DATED : June 21, 2022
INVENTOR(S) : Yoshiyuki Fukuhara et al.

It is certified that error appears in the above-identified patent and that said Letters Patent is hereby corrected as shown below:

On the Title Page

Item (30), in Column 1, in "Foreign Application Priority Data", Line 1, delete "(WO)" and insert -- (JP) --.

Item (30), in Column 1, in "Foreign Application Priority Data", Line 2, delete "(WO)" and insert -- (JP) --.

Item (30), in Column 1, in "Foreign Application Priority Data", Line 3, delete "(WO)" and insert -- (JP) --.

In the Specification

In Column 23, Line 39, delete "lain" and insert -- 1a in --.

Signed and Sealed this
Twenty-third Day of August, 2022

Katherine Kelly Vidal
Director of the United States Patent and Trademark Office